United States Patent
Cassayre et al.

(10) Patent No.: US 11,388,902 B2
(45) Date of Patent: Jul. 19, 2022

(54) PESTICIDALLY ACTIVE CYCLOPROPYL METHYL AMIDE DERIVATIVES

(71) Applicant: SYNGENTA PARTICIPATIONS AG, Basel (CH)

(72) Inventors: Jérôme Yves Cassayre, Stein (CH); Myriem El Qacemi, Stein (CH); Thomas Pitterna, Stein (CH); André Stoller, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/496,195

(22) PCT Filed: Mar. 22, 2018

(86) PCT No.: PCT/EP2018/057333
§ 371 (c)(1),
(2) Date: Sep. 20, 2019

(87) PCT Pub. No.: WO2018/172471
PCT Pub. Date: Sep. 27, 2018

(65) Prior Publication Data
US 2020/0045973 A1    Feb. 13, 2020

(30) Foreign Application Priority Data
Mar. 22, 2017 (EP) ................ 17162226

(51) Int. Cl.
*A01N 43/80* (2006.01)
*C07D 261/04* (2006.01)

(52) U.S. Cl.
CPC ........... *A01N 43/80* (2013.01); *C07D 261/04* (2013.01)

(58) Field of Classification Search
CPC .............................. C07D 261/04; A01N 43/80
See application file for complete search history.

(56) References Cited

U.S. PATENT DOCUMENTS

| | | | |
|---|---|---|---|
| 9,968,087 B2 * | 5/2018 | Bindschaedler | A01N 43/82 |
| 10,045,969 B2 | 8/2018 | Mita et al. | |
| 2016/0366887 A1 * | 12/2016 | Bindschaedler | A01N 43/54 |

FOREIGN PATENT DOCUMENTS

| | | |
|---|---|---|
| EP | 1731512 A1 | 12/2006 |
| EP | 2172448 A1 | 4/2010 |
| JP | 2010529989 A | 9/2010 |
| WO | 2005085216 A | 3/2005 |
| WO | 2008154528 A2 | 12/2008 |
| WO | 2012149236 A1 | 11/2012 |
| WO | 2014008214 A1 | 1/2014 |
| WO | 2015128358 A1 | 9/2015 |

OTHER PUBLICATIONS

Written Opinion & International Search Report for International Application No. PCT/EP2018/057333 dated Jul. 25, 2018.
Annex of CAS Registry Compounds from Japanese Office Action dated Dec. 22, 2021.
Official Action in corresponding JP Application No. 2019-552209, dispatched on Dec. 22, 2021, and English translation of Examiner's comments.

* cited by examiner

*Primary Examiner* — Kamal A Saeed
(74) *Attorney, Agent, or Firm* — BakerHostetler; Toni-Junell Herbert

(57) ABSTRACT

The present invention relates to compounds of formula (I) wherein the substituents are as defined in claim 1, and the agrochemically acceptable salts, stereoisomers, enantiomers, tautomers and N-oxides of those compounds; to intermediates for preparing compounds of formula (I), to compositions comprising them and to methods of using them to combat and control insect, acarine, nematode and mollusc pests.

19 Claims, No Drawings

PESTICIDALLY ACTIVE CYCLOPROPYL METHYL AMIDE DERIVATIVES

CROSS-REFERENCE TO RELATED APPLICATIONS

This application is a 371 National Stage application of International Application No. PCT/EP2018/057333, filed Mar. 22, 2018, which claims priority to EP 17162226.9, filed Mar. 22, 2017, the entire contents of which applications are hereby incorporated by reference.

The present invention relates to pesticidally active, in particular insecticidally active cyclopropyl methyl amide isoxazolines, to compositions comprising those compounds, and to their use for controlling animal pests (including arthropods and in particular insects or representatives of the order Acarina).

Certain isoxazoline derivatives with insecticidal properties are disclosed, for example, in WO 2011/067272.

There have now been found novel pesticidally active cyclopropyl methyl amide isoxazoline derivatives.

The present invention accordingly relates to compounds of formula (I), (I)

wherein
$A^1$, $A^2$, $A^3$ and $A^4$, independently of one another, are C—H, C—$R^5$ or nitrogen;
$R^1$ is hydrogen, $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl,
$C_1$-$C_8$dialkylaminocarbonyloxy$C_1$-$C_8$alkyl,
$C_1$-$C_8$alkylaminocarbonyl$C_1$-$C_8$alkyl,
$C_1$-$C_8$dialkylaminocarbonyl$C_1$-$C_8$alkyl or
$C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group;
$R^2$ is cyano, C(S)$NH_2$ or C(O)$NH_2$;
$R^3$ is $C_1$-$C_8$haloalkyl;
$R^4$ is aryl, aryl substituted by one to three $R^7$, heteroaryl or heteroaryl substituted by one to three $R^7$;
$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH═CH—CH═CH— bridge, a —$CH_2$—$CH_2$—$CH_2$— bridge, a —CH(OH)—$CH_2$—$CH_2$— bridge, a —C(O)—$CH_2$—$CH_2$— bridge or a —N═CH—CH═CH— bridge;
$R^6$ is hydrogen or $C_1$-$C_8$alkyl; and
$R^7$ is independently halogen, cyano, nitro, $C_1$-$C_8$alkyl, $C_1$-$C_8$haloalkyl, $C_1$-$C_8$alkoxy, $C_1$-$C_8$haloalkoxy;

and agrochemically acceptable salts, stereoisomers, enantiomers, tautomers and N-oxides of those compounds.

Compounds of formula (I) which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, but are not limited to, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkylcarbonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, but is not limited to, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Examples of Alkoxy include, but are not limited to, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms. Examples of Alkoxyalkyl include, but are not limited to, methoxymethyl, methoxyethyl, ethoxymethyl, ethoxyethyl, n-propoxymethyl, n-propoxyethyl, isopropoxymethyl or isopropoxyethyl.

Examples of Alkoxycarbonyl include, but are not limited to, methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms and are, for example, cyclopropyl, cyclobutyl, cyclopentyl and cyclohexyl.

As used herein, the term "$C_2$-$C_8$alkynyl" refers to a straight or branched hydrocarbon chain radical group consisting solely of carbon and hydrogen atoms, containing at least one triple bond, having from two to eight carbon atoms, and which is attached to the rest of the molecule by a single bond. Examples of $C_2$-$C_8$ alkynyl include, but are not limited to, ethynyl, prop-1-ynyl, but-1-ynyl and but-2-ynyl.

As used herein, the term "$C_2$-$C_8$alkenyl" refers to a straight or branched hydrocarbon chain radical group consisting solely of carbon and hydrogen atoms, containing at least one double bond, having from two to eight carbon atoms, and which is attached to the rest of the molecule by a single bond. Examples of $C_2$-$C_8$alkenyl include, but are not limited to, prop-1-enyl, but-1-enyl and but-2-enyl.

As used herein, alkylcarbonyloxyalkyl refers to a group —ROC(O)R, wherein each R is, independently, $C_1$-$C_8$ alkyl.

As used herein, alkoxycarbonylsulfanyl refers to a group —SC(O)OR, wherein R is $C_1$-$C_8$ alkyl.

As used herein, alkylaminocarbonyloxyalkyl refers to a group —ROC(O)NHR, wherein each R is, independently, $C_1$-$C_8$ alkyl.

As used herein, dialkylaminocarbonyloxyalkyl refers to a group —ROC(O)NRR, wherein each R is, independently, $C_1$-$C_8$ alkyl.

As used herein, alkylaminocarbonylalkyl refers to a group —RC(O)NHR, wherein each R is, independently, $C_1$-$C_8$ alkyl.

As used herein, dialkylaminocarbonylalkyl refers to a group —RC(O)NRR, wherein each R is, independently, $C_1$-$C_8$ alkyl.

As used herein, alkoxycarbonylalkylaminoalkyl refers to a group —RNH(R)C(O)OR, wherein each R is, independently, $C_1$-$C_8$ alkyl.

The compounds of formula (I) according to the invention also include hydrates which may be formed during the salt formation.

Preferred values of $A^1$, $A^2$, $A^3$, $A^4$, $R^1$, $R^2$, $R^3$, $R^4$, $R^5$, $R^6$ and $R^7$ are, in any combination, as set out below.

Preferably at least two of $A^1$, $A^2$, $A^3$ and $A^4$ are different from nitrogen.

Preferably $A^1$ is C—H or C—$R^5$; more preferably $A^1$ is C—$R^5$.

Preferably $A^2$ is C—H or C—$R^5$; more preferably $A^2$ is C—H.

Preferably $A^3$ is C—H or N; more preferably $A^3$ is C—H.
Preferably $A^4$ is C—H or N; more preferably $A^4$ is C—H.

In a preferred embodiment $A^1$ is N, C—H or C—$R^5$, $A^2$ is C—H, $A^3$ is C—H or N and $A^4$ is C—H.

In a preferred embodiment of the invention, $R^1$ is hydrogen, $C_1$-$C_8$alkyl, $C_1$-$C_8$alkylcarbonyl- or $C_1$-$C_8$alkoxycarbonyl; $R^2$ is cyano, C(S)$NH_2$ or C(O)$NH_2$; $R^3$ is $C_1$-$C_4$haloalkyl; $R^4$ is aryl, aryl substituted by one to three $R^7$, 5-6 membered heteroaryl or 5-6 membered heteroaryl substituted by one to three $R^7$; $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl; $R^7$ is independently halogen, cyano, $C_1$-$C_4$alkyl, $C_1$-$C_4$haloalkyl, $C_1$-$C_4$alkoxy or $C_1$-$C_4$haloalkoxy.

In a more preferred embodiment, $R^1$ is hydrogen, methyl, ethyl, methylcarbonyl-, or methoxycarbonyl; $R^2$ is cyano, C(S)$NH_2$ or C(O)$NH_2$; $R^3$ is chlorodifluoromethyl or trifluoromethyl; $R^4$ is aryl or aryl substituted by one to three $R^7$; $R^5$ is independently halogen, cyano, nitro, $C_1$-$C_8$alkyl, $C_2$-$C_8$ alkenyl, $C_3$-$C_8$cycloalkyl, or $C_1$-$C_8$haloalkyl; $R^7$ is independently methyl, fluoro, chloro, bromo, trifluoromethyl, trifluoromethoxy, cyano or methoxy.

In an even more preferred embodiment, $R^1$ is hydrogen, methyl or ethyl; especially hydrogen or methyl; more especially hydrogen; $R^2$ is cyano, C(S)$NH_2$ or C(O)$NH_2$; $R^3$ is trifluoromethyl; $R^4$ is phenyl or phenyl substituted by one to three $R^7$; even more preferably $R^4$ is phenyl substituted by one to three $R^7$; $R^5$ is independently bromo, chloro, fluoro, cyano, nitro, methyl, ethyl, trifluoromethyl, cyclopropyl, or vinyl; $R^7$ is independently Cl, Br, F, $CF_3$, $CH_3$, $OCF_3$ or $OCH_3$.

In a most preferred embodiment, $R^1$ is especially hydrogen or methyl; preferably hydrogen; $R^2$ is cyano, C(S)$NH_2$ or C(O)$NH_2$; $R^3$ is trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; preferably $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl, or 3,4,5-trichloro-phenyl; $R^5$ is independently bromo, chloro, fluoro, cyclopropyl, trifluoromethyl, vinyl, or methyl; preferably chloro, bromo, cyclopropyl, or methyl.

In another embodiment of the invention, $R^1$ is $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group; $R^2$ is cyano, C(S)$NH_2$ or C(O)$NH_2$; $R^3$ is $C_1$-$C_4$haloalkyl; $R^4$ is aryl, aryl substituted by one to three $R^7$, 5-6 membered heteroaryl or 5-6 membered heteroaryl substituted by one to three $R^7$; $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl; $R^7$ is independently halogen, cyano, $C_1$-$C_4$alkyl, $C_1$-$C_4$haloalkyl, $C_1$-$C_4$alkoxy or $C_1$-$C_4$haloalkoxy.

In a more preferred embodiment, $R^1$ is $C_1$-$C_8$alkyl, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, wherein each alkyl or alkoxy group may be optionally substituted with from one to three halogen atoms or with a cyano group; $R^2$ is cyano, C(S)$NH_2$ or C(O)$NH_2$; $R^3$ is chlorodifluoromethyl or trifluoromethyl; $R^4$ is aryl or aryl substituted by one to three $R^7$; $R^5$ is independently halogen, cyano, nitro, $C_1$-$C_8$alkyl, $C_2$-$C_8$ alkenyl, $C_3$-$C_8$cycloalkyl, or $C_1$-$C_8$haloalkyl; $R^7$ is independently methyl, fluoro, chloro, bromo, trifluoromethyl, trifluoromethoxy, cyano or methoxy.

In an even more preferred embodiment, $R^1$ is $C_1$-$C_8$cyanoalkyl, $C_1$-$C_8$alkoxy-$C_1$-$C_8$alkyl, $C_1$-$C_8$alkoxycarbonyl or $C_1$-$C_8$alkylcarbonyloxy$C_1$-$C_8$alkyl; $R^2$ is cyano, C(S)$NH_2$ or C(O)$NH_2$; $R^3$ is trifluoromethyl; $R^4$ is phenyl or phenyl substituted by one to three $R^7$; even more preferably $R^4$ is phenyl substituted by one to three $R^7$; $R^5$ is independently bromo, chloro, fluoro, cyano, nitro, methyl, ethyl, trifluoromethyl, cyclopropyl, or vinyl; $R^7$ is independently Cl, Br, F, $CF_3$, $CH_3$, $OCF_3$ or $OCH_3$.

In a most preferred embodiment, $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^2$ is cyano, C(S)$NH_2$ or C(O)$NH_2$; $R^3$ is trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; preferably $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl, or 3,4,5-trichloro-phenyl; $R^5$ is independently bromo, chloro, fluoro, cyclopropyl, trifluoromethyl, vinyl, or methyl; preferably chloro, bromo, cyclopropyl, or methyl.

EMBODIMENT E1

In a preferred embodiment of the invention, $R^1$ is hydrogen, $C_1$-$C_8$alkyl, $C_1$-$C_8$alkylcarbonyl- or $C_1$-$C_8$alkoxycarbonyl; more preferably hydrogen, methyl, ethyl, methylcarbonyl-, or methoxycarbonyl; most preferably hydrogen, methyl or ethyl; especially hydrogen or methyl; more especially hydrogen.

EMBODIMENT E1-1

In a preferred embodiment of the invention, preferably $R^1$ is $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group, preferably $R^1$ is $C_1$-$C_8$cyanoalkyl, $C_1$-$C_8$alkoxy-$C_1$-$C_8$alkyl, $C_1$-$C_8$alkoxycarbonyl or $C_1$-$C_8$alkylcarbonyloxy$C_1$-$C_8$alkyl and most preferably $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl.

EMBODIMENT E2

In a preferred embodiment of the invention, preferably $R^2$ is cyano.

EMBODIMENT E2-1

In a preferred embodiment of the invention, preferably $R^2$ is $C(S)NH_2$.

EMBODIMENT E2-2

In a preferred embodiment of the invention, preferably $R^2$ is $C(O)NH_2$.

EMBODIMENT E3

In a preferred embodiment of the invention, preferably $R^3$ is $C_1$-$C_4$haloalkyl; more preferably chlorodifluoromethyl or trifluoromethyl; most preferably trifluoromethyl.

EMBODIMENT E4

In a preferred embodiment of the invention, preferably $R^4$ is aryl, aryl substituted by one to three $R^7$, 5-6 membered heteroaryl or 5-6 membered heteroaryl substituted by one to three $R^7$; more preferably $R^4$ is aryl or aryl substituted by one to three $R^7$; most preferably phenyl or phenyl substituted by one to three $R^7$; even more preferably $R^4$ is phenyl substituted by one to three $R^7$; especially $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl, or 3,4,5-trichloro-phenyl.

EMBODIMENT E5

In a preferred embodiment of the invention, preferably $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl; more preferably halogen, cyano, nitro, $C_1$-$C_8$alkyl, $C_2$-$C_8$ alkenyl, $C_3$-$C_8$cycloalkyl, or $C_1$-$C_8$haloalkyl; even more preferably bromo, chloro, fluoro, cyano, nitro, methyl, ethyl, trifluoromethyl, cyclopropyl, or vinyl; yet even more preferably bromo, chloro, fluoro, cyclopropyl, trifluoromethyl, vinyl, or methyl; most preferably chloro, bromo, or methyl.

EMBODIMENT E6

In a preferred embodiment of the invention, preferably $R^7$ is independently halogen, cyano, $C_1$-$C_4$alkyl, $C_1$-$C_4$haloalkyl, $C_1$-$C_4$alkoxy or $C_1$-$C_4$haloalkoxy; more preferably methyl, fluoro, chloro, bromo, trifluoromethyl, trifluoromethoxy, cyano or methoxy, even more preferably $R^7$ is Cl, Br, F, $CF_3$, $CH_3$, $OCF_3$ or $OCH_3$.

Each of the Embodiments E1 to E6 can be combined to a new preferred group of compounds of formula (I) as shown in the following Table E.

TABLE E preferred embodiments of the formula (I):

| Combination | Combination | Combination | Combination | Combination |
|---|---|---|---|---|
| E1 + E2 | E3 + E6 | E1 + E4 + E5 | E1 + E2 + E3 + E6 | E1 + E2 + E3 + E5 |
| E1 + E3 | E4 + E5 | E1 + E4 + E6 | E1 + E2 + E4 + E6 | E1 + E2 + E4 + E5 |
| E1 + E4 | E4 + E6 | E1 + E5 + E6 | E1 + E2 + E5 + E6 | E1 + E3 + E4 + E5 |
| E1 + E5 | E5 + E6 | E2 + E3 + E4 | E1 + E3 + E4 + E6 | E2 + E3 + E4 + E5 |
| E1 + E6 | E1 + E2 + E3 | E2 + E3 + E5 | E1 + E3 + E5 + E6 | E1 + E2 + E3 + E4 + E5 |
| E2 + E3 | E1 + E2 + E4 | E2 + E3 + E6 | E1 + E4 + E5 + E6 | E1 + E2 + E3 + E5 + E6 |
| E2 + E4 | E1 + E2 + E5 | E2 + E4 + E5 | E2 + E3 + E5 + E6 | E1 + E2 + E3 + E4 + E5 + E6 |
| E2 + E5 | E1 + E2 + E6 | E2 + E4 + E6 | E1 + E2 + E3 + E4 | |
| E2 + E6 | E1 + E3 + E4 | E2 + E5 + E6 | E2 + E3 + E4 + E6 | |
| E3 + E4 | E1 + E3 + E5 | E3 + E4 + E6 | E2 + E4 + E5 + E6 | |
| E3 + E5 | E1 + E3 + E6 | E3 + E5 + E6 | E3 + E4 + E5 + E6 | |

Table E-1: Preferred Embodiments of the Formula (I)

Each of the Embodiments E1 to E6 can be combined to a new preferred group of compounds of formula (I) as shown in the Table E but E1 has the meaning of the Embodiment E1-1.

Table E-2: Preferred Embodiments of the Formula (I)

Each of the Embodiments E1 to E6 can be combined to a new preferred group of compounds of formula (I) as shown in the Table E but E2 has the meaning of the Embodiment E2-1.

Table E-3: Preferred Embodiments of the Formula (I)

Each of the Embodiments E1 to E6 can be combined to a new preferred group of compounds of formula (I) as shown in the Table E but E2 has the meaning of the Embodiment E2-2.

Table E-4: Preferred Embodiments of the Formula (I)

Each of the Embodiments E1 to E6 can be combined to a new preferred group of compounds of formula (I) as shown in the Table E but E1 has the meaning of the Embodiment E1-1 and E2 has the meaning of the Embodiment E2-1.

Table E-5: Preferred Embodiments of the Formula (I)

Each of the Embodiments E1 to E6 can be combined to a new preferred group of compounds of formula (I) as shown in the Table E but E1 has the meaning of Embodiment E1-1 and E2 has the meaning of the Embodiment E2-2.

In all of the preferred embodiments mentioned above and the combinations of Table E, $R^6$ is preferably hydrogen.

In all of the preferred embodiments mentioned above and the combinations of Table E, $A^1$ is preferably N, C—H or C—$R^5$, $A^2$ preferably is C—H, $A^3$ is preferably C—H or N and $A^4$ is preferably C—H.

More preferably in all of the preferred embodiments mentioned above and the combinations of Table E, $A^1$ is preferably C—$CH_3$, $A^2$ is preferably C—H, $A^3$ is preferably C—H and $A^4$ is preferably C—H.

The compounds of the invention may be made by a variety of methods as shown in Schemes 1 to 5.

1) Compounds of formula (I) can be prepared by reacting a compound of formula (II) wherein R is OH, $C_1$-$C_6$alkoxy or Cl, F or Br, with an amine of formula (III), wherein $R^6$ is H or $C_1$-$C_8$alkyl and $R^2$ is cyano, $C(S)NH_2$ or $C(O)NH_2$, as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO 2009/080250.

3) Carboxylic acids of formula (II), wherein R is OH, may be formed from esters of formula (II), wherein R is $C_1$-$C_6$alkoxy as described for example in WO 2009/080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropyl-ethylamine (Hunig's base), in a solvent, such as water, N,N-dimethyl-

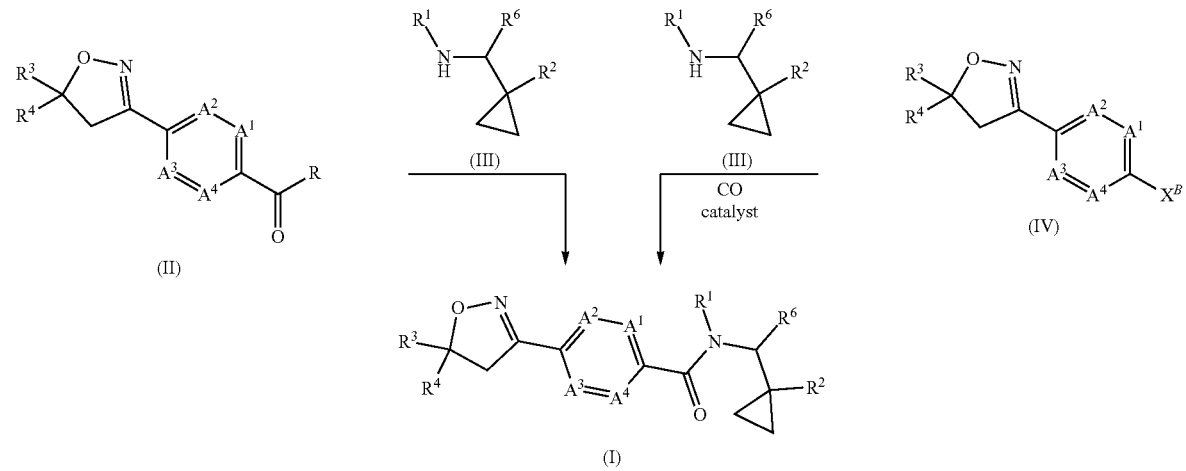

Scheme 1 formamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO 2009/080250.

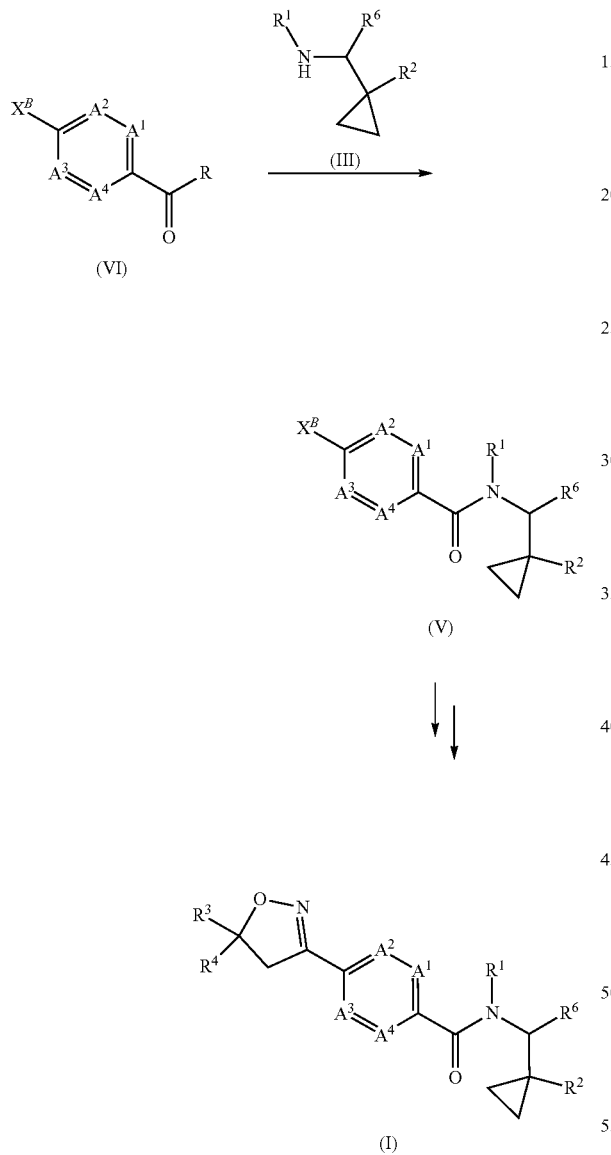

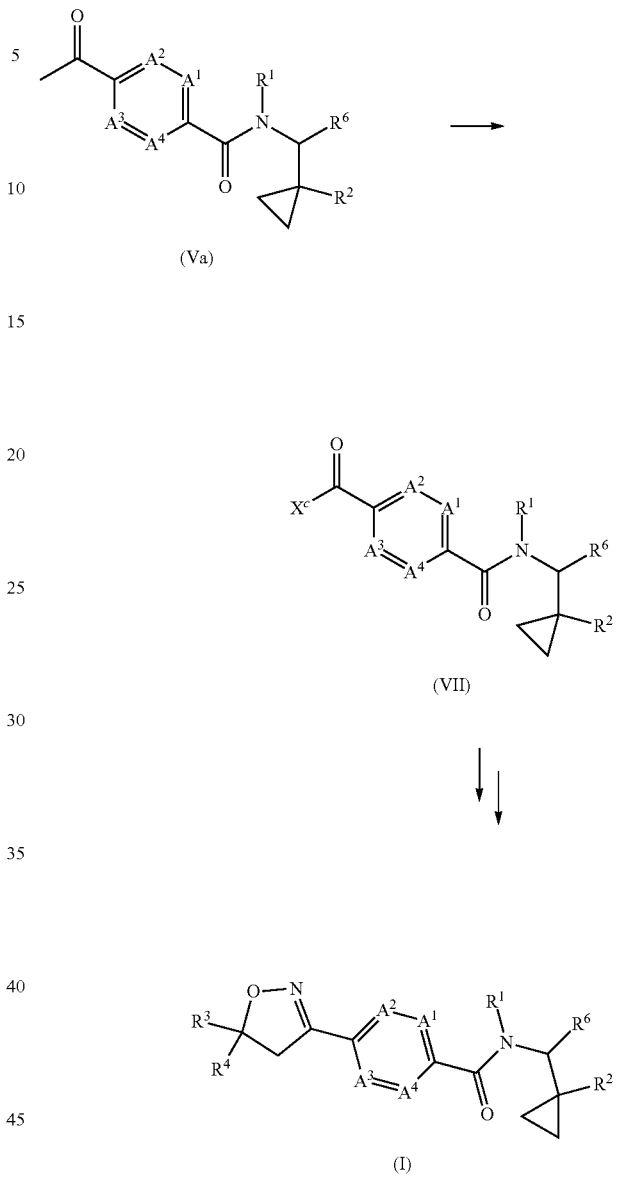

6) Alternatively, compounds of formula (I), wherein $R^6$ is H or $C_1$-$C_8$alkyl and $R^2$ is cyano, C(S)NH$_2$ or C(O)NH$_2$, can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO 2009/080250. An intermediate of formula (V) can be prepared for example from an intermediate of formula (VI) as described in the same reference.

7) Alternatively, compounds of formula (I) can be prepared by various methods from an intermediate of formula (VII) as shown in Scheme 3 wherein $X^C$ is CH=C($R^3$)$R^4$, or CH$_2$C(OH)($R^3$)$R^4$ wherein $R^3$ and $R^4$ are as defined for a compound of formula (I) according to similar methods to those described in WO 2009/080250.

8) Compounds of formula (VII) wherein $X^C$ is CH=C($R^3$)$R^4$, or CH$_2$C(OH)($R^3$)$R^4$ can be prepared from a compound of formula (Va) or from a compound of formula (VII) wherein $X^C$ is CH$_2$-halogen using similar methods to those described in WO 2009/080250.

9) Compounds of formula (VII) wherein $X^C$ is CH$_2$-halogen, such as bromo or chloro, can be prepared by reacting a methyl ketone of formula (Va), with a halogenating agent, such as bromine or chlorine, in a solvent, such as acetic acid, at a temperature of from 0° C. to 50° C., preferably from ambient temperature to 40° C.

Scheme 4

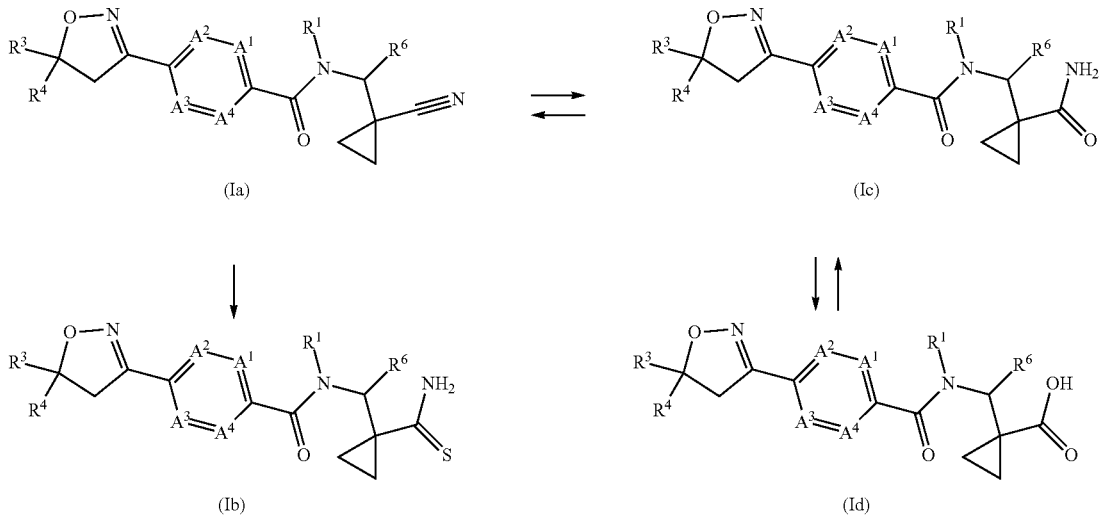

10) Compounds of formula (Ic) can be prepared by reacting a compound of formula (Ia) as shown in Scheme 4. Such reactions are usually carried out in the presence of an acid, such as sulfuric acid, or a base, such as sodium hydroxide, or even hydrogen peroxide, using methods known to a person skilled in the art.

11) In addition, Compounds of formula (Ia) can be prepared by reacting a compound of formula (Ic) as shown in Scheme 4. Such reactions are usually carried out in the presence of a dehydrating agent, such as trifluoroacetic anhydride or phosphorus(V) oxide, using methods known to a person skilled in the art.

12) Compounds of formula (Ib) can be prepared by reacting a compound of formula (Ia) as shown in Scheme 4. Such reactions are usually carried out in the presence of a thionating agent, such as phosphorus pentasulfide or Lawesson's reagent or $H_2S$ or ammonium sulfide, using methods known to a person skilled in the art.

13) Compounds of formula (Id) can be prepared by reacting a compound of formula (Ic) as indicated in 10).

14) Compounds of formula (Ic) can be prepared by reacting a compound of formula (Id) with ammonia, using methods known to a person skilled in the art.

Scheme 5

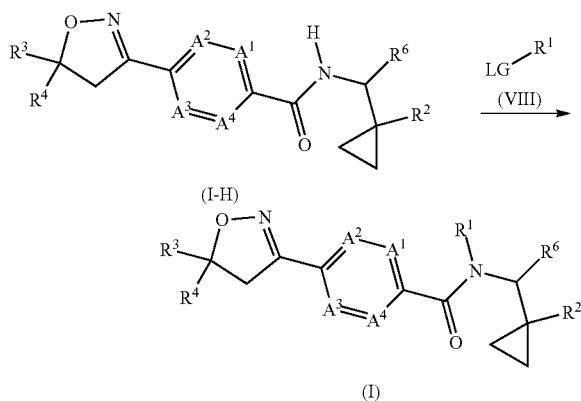

15) Compounds of formula (I) can be prepared by reacting a compound of formula (I-H) with a compound of formula (VIII) where LG is a suitable leaving group, for example a halogen, such as bromo or chloro, or an imidazole or an alkylsulfoxy group or a haloalkylsulfoxy group or an arylsulfoxy group, as shown in Scheme 5. Such reactions are usually carried out in the presence of a base, such as sodium hydroxide or sodium hydride, using methods known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention. Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

The present invention also provides intermediates useful for the preparation of compounds of formula (I). Certain intermediates are novel and as such form a further aspect of the invention. One group of novel intermediates are compounds of formula (Int-I)

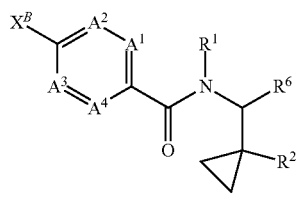

(Int-I)

wherein $A^1$, $A^2$, $A^3$, $A^4$, $R^1$ and $R^6$ are as defined for a compound of formula (I) and $X^B$ is a halogen, such as bromo, or $X^B$ is cyano, formyl, CH=N—OH or acetyl; $R^2$ is cyano, C(S)NH$_2$, C(O)OH or C(O)NH$_2$; and a salt or N-oxide thereof. The preferences for $A^1$, $A^2$, $A^3$, $A^4$ and $R^1$ are the same as the preferences set out for the corresponding substituents of a compound of formula (I).

Another group of novel intermediates are compounds of formula (Int-II)

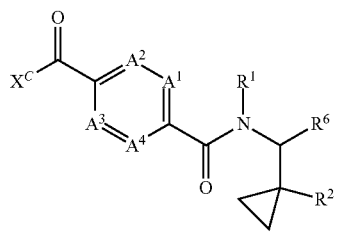

(Int-II)

wherein $A^1$, $A^2$, $A^3$, $A^4$, $R^1$ and $R^6$ are as defined for a compound of formula (I); $R^2$ is cyano, C(S)NH$_2$, C(O)OH or C(O)NH$_2$; $X^C$ is CH$_2$-halogen, wherein halogen is e.g. bromo or chloro, CH=C(R$^3$)R$^4$ or CH$_2$C(OH)(R$^3$)R$^4$ wherein $R^3$ and $R^4$ are as defined for a compound of formula (I); and a salt or N-oxide thereof. The preferences for $A^1$, $A^2$, $A^3$, $A^4$, $R^1$ and $R^6$ are the same as the preferences set out for the corresponding substituents of a compound of formula (I).

Another group of novel intermediates are compounds of formula (Int-III)

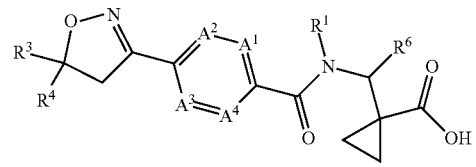

(Int-III)

wherein $A^1$, $A^2$, $A^3$, $A^4$, $R^1$, $R^3$, $R^4$ and $R^6$ are as defined for a compound of formula (I); and a salt or N-oxide thereof. The preferences for $A^1$, $A^2$, $A^3$, $A^4$, $R^1$, $R^3$, $R^4$ and $R^6$ are the same as the preferences set out for the corresponding substituents of a compound of formula (I).

The compounds of formula (I) and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

Compounds of formula (I) include at least one chiral centre and may exist as compounds of formula (I*) or compounds of formula (I**):

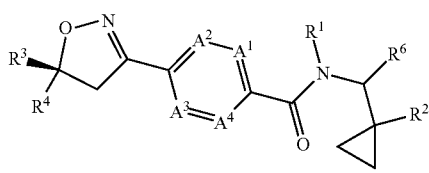

(I*)

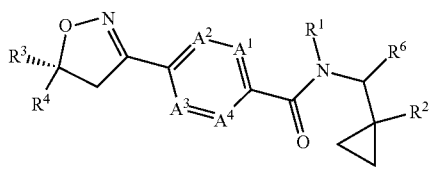

(I**)

Generally compounds of formula (I**) are more biologically active than compounds of formula (I*). The invention includes mixtures of compounds (I*) and (I) in any ratio e.g. in a molar ratio of 1:99 to 99:1, e.g. 10:1 to 1:10, e.g. a substantially 50:50 molar ratio. In an enantiomerically (or epimerically) enriched mixture of formula (I), the molar proportion of compound (I**) compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula (I*), the molar proportion of the compound of formula (I*) compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula (I**) are preferred.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties, can be obtained in free form or in the form of salts.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 162 below can be prepared according to the methods described above. The examples which follow are intended to illustrate the invention and show preferred compounds of formula (I).

Tables 1 to 54: Compounds of Formula (Ia)

The invention is further illustrated by making available the following individual compounds of formula (Ia) listed below in Tables 1 to 54.

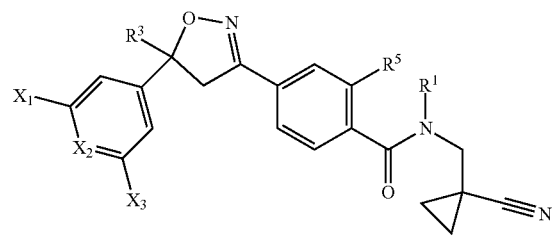

(Ia)

Each of Tables 1 to 54, which follow the Table P below, make available 250 compounds of the formula (Ia) in which $X_3$, $R^3$, $X_1$ and $R^5$ are the substituents defined in Table P and $R^1$ and $X_2$ are the substituents defined in the relevant Table 1 to 54. Thus Table 1 individualizes 250 compounds of formula (Ia) wherein for each row of Table P, the $R^1$ and $X_2$ substituent are as defined in Table 1; similarly, Table 2 individualizes 250 compounds of formula (Ia) wherein for each row of Table P, the $R^1$ and $X_2$ substituent are as defined in Table 2; and so on for Tables 3 to 54.

Each compound disclosed in Tables 1 to 54 represents a disclosure of a compound according to the compound of formula (I*), and a disclosure according to the compound of formula (I**) as well as mixtures thereof.

TABLE P

| | $X_3$ | $R^3$ | $X_1$ | $R^5$ |
|---|---|---|---|---|
| 1 | H | $CF_3$ | H | Me |
| 2 | Cl | $CF_3$ | H | Me |
| 3 | Br | $CF_3$ | H | Me |
| 4 | F | $CF_3$ | H | Me |
| 5 | $CF_3$ | $CF_3$ | H | Me |
| 6 | H | $CF_2Cl$ | H | Me |
| 7 | Cl | $CF_2Cl$ | H | Me |
| 8 | Br | $CF_2Cl$ | H | Me |
| 9 | F | $CF_2Cl$ | H | Me |
| 10 | $CF_3$ | $CF_2Cl$ | H | Me |
| 11 | H | $CF_3$ | Cl | Me |
| 12 | Cl | $CF_3$ | Cl | Me |
| 13 | Br | $CF_3$ | Cl | Me |
| 14 | F | $CF_3$ | Cl | Me |
| 15 | $CF_3$ | $CF_3$ | Cl | Me |
| 16 | H | $CF_2Cl$ | Cl | Me |
| 17 | Cl | $CF_2Cl$ | Cl | Me |
| 18 | Br | $CF_2Cl$ | Cl | Me |
| 19 | F | $CF_2Cl$ | Cl | Me |
| 20 | $CF_3$ | $CF_2Cl$ | Cl | Me |
| 21 | H | $CF_3$ | Br | Me |

TABLE P-continued

| | X$_3$ | R$^3$ | X$_1$ | R$^5$ |
|---|---|---|---|---|
| 22 | Cl | CF$_3$ | Br | Me |
| 23 | Br | CF$_3$ | Br | Me |
| 24 | F | CF$_3$ | Br | Me |
| 25 | CF$_3$ | CF$_3$ | Br | Me |
| 26 | H | CF$_2$Cl | Br | Me |
| 27 | Cl | CF$_2$Cl | Br | Me |
| 28 | Br | CF$_2$Cl | Br | Me |
| 29 | F | CF$_2$Cl | Br | Me |
| 30 | CF$_3$ | CF$_2$Cl | Br | Me |
| 31 | H | CF$_3$ | F | Me |
| 32 | Cl | CF$_3$ | F | Me |
| 33 | Br | CF$_3$ | F | Me |
| 34 | F | CF$_3$ | F | Me |
| 35 | CF$_3$ | CF$_3$ | F | Me |
| 36 | H | CF$_2$Cl | F | Me |
| 37 | Cl | CF$_2$Cl | F | Me |
| 38 | Br | CF$_2$Cl | F | Me |
| 39 | F | CF$_2$Cl | F | Me |
| 40 | CF$_3$ | CF$_2$Cl | F | Me |
| 41 | H | CF$_3$ | CF$_3$ | Me |
| 42 | Cl | CF$_3$ | CF$_3$ | Me |
| 43 | Br | CF$_3$ | CF$_3$ | Me |
| 44 | F | CF$_3$ | CF$_3$ | Me |
| 45 | CF$_3$ | CF$_3$ | CF$_3$ | Me |
| 46 | H | CF$_2$Cl | CF$_3$ | Me |
| 47 | Cl | CF$_2$Cl | CF$_3$ | Me |
| 48 | Br | CF$_2$Cl | CF$_3$ | Me |
| 49 | F | CF$_2$Cl | CF$_3$ | Me |
| 50 | CF$_3$ | CF$_2$Cl | CF$_3$ | Me |
| 51 | H | CF$_3$ | H | Cl |
| 52 | Cl | CF$_3$ | H | Cl |
| 53 | Br | CF$_3$ | H | Cl |
| 54 | F | CF$_3$ | H | Cl |
| 55 | CF$_3$ | CF$_3$ | H | Cl |
| 56 | H | CF$_2$Cl | H | Cl |
| 57 | Cl | CF$_2$Cl | H | Cl |
| 58 | Br | CF$_2$Cl | H | Cl |
| 59 | F | CF$_2$Cl | H | Cl |
| 60 | CF$_3$ | CF$_2$Cl | H | Cl |
| 61 | H | CF$_3$ | Cl | Cl |
| 62 | Cl | CF$_3$ | Cl | Cl |
| 63 | Br | CF$_3$ | Cl | Cl |
| 64 | F | CF$_3$ | Cl | Cl |
| 65 | CF$_3$ | CF$_3$ | Cl | Cl |
| 66 | H | CF$_2$Cl | Cl | Cl |
| 67 | Cl | CF$_2$Cl | Cl | Cl |
| 68 | Br | CF$_2$Cl | Cl | Cl |
| 69 | F | CF$_2$Cl | Cl | Cl |
| 70 | CF$_3$ | CF$_2$Cl | Cl | Cl |
| 71 | H | CF$_3$ | Br | Cl |
| 72 | Cl | CF$_3$ | Br | Cl |
| 73 | Br | CF$_3$ | Br | Cl |
| 74 | F | CF$_3$ | Br | Cl |
| 75 | CF$_3$ | CF$_3$ | Br | Cl |
| 76 | H | CF$_2$Cl | Br | Cl |
| 77 | Cl | CF$_2$Cl | Br | Cl |
| 78 | Br | CF$_2$Cl | Br | Cl |
| 79 | F | CF$_2$Cl | Br | Cl |
| 80 | CF$_3$ | CF$_2$Cl | Br | Cl |
| 81 | H | CF$_3$ | F | Cl |
| 82 | Cl | CF$_3$ | F | Cl |
| 83 | Br | CF$_3$ | F | Cl |
| 84 | F | CF$_3$ | F | Cl |
| 85 | CF$_3$ | CF$_3$ | F | Cl |
| 86 | H | CF$_2$Cl | F | Cl |
| 87 | Cl | CF$_2$Cl | F | Cl |
| 88 | Br | CF$_2$Cl | F | Cl |
| 89 | F | CF$_2$Cl | F | Cl |
| 90 | CF$_3$ | CF$_2$Cl | F | Cl |
| 91 | H | CF$_3$ | CF$_3$ | Cl |
| 92 | Cl | CF$_3$ | CF$_3$ | Cl |
| 93 | Br | CF$_3$ | CF$_3$ | Cl |
| 94 | F | CF$_3$ | CF$_3$ | Cl |
| 95 | CF$_3$ | CF$_3$ | CF$_3$ | Cl |
| 96 | H | CF$_2$Cl | CF$_3$ | Cl |
| 97 | Cl | CF$_2$Cl | CF$_3$ | Cl |
| 98 | Br | CF$_2$Cl | CF$_3$ | Cl |
| 99 | F | CF$_2$Cl | CF$_3$ | Cl |
| 100 | CF$_3$ | CF$_2$Cl | CF$_3$ | Cl |
| 101 | H | CF$_3$ | H | Br |
| 102 | Cl | CF$_3$ | H | Br |
| 103 | Br | CF$_3$ | H | Br |
| 104 | F | CF$_3$ | H | Br |
| 105 | CF$_3$ | CF$_3$ | H | Br |
| 106 | H | CF$_2$Cl | H | Br |
| 107 | Cl | CF$_2$Cl | H | Br |
| 108 | Br | CF$_2$Cl | H | Br |
| 109 | F | CF$_2$Cl | H | Br |
| 110 | CF$_3$ | CF$_2$Cl | H | Br |
| 111 | H | CF$_3$ | Cl | Br |
| 112 | Cl | CF$_3$ | Cl | Br |
| 113 | Br | CF$_3$ | Cl | Br |
| 114 | F | CF$_3$ | Cl | Br |
| 115 | CF$_3$ | CF$_3$ | Cl | Br |
| 116 | H | CF$_2$Cl | Cl | Br |
| 117 | Cl | CF$_2$Cl | Cl | Br |
| 118 | Br | CF$_2$Cl | Cl | Br |
| 119 | F | CF$_2$Cl | Cl | Br |
| 120 | CF$_3$ | CF$_2$Cl | Cl | Br |
| 121 | H | CF$_3$ | Br | Br |
| 122 | Cl | CF$_3$ | Br | Br |
| 123 | Br | CF$_3$ | Br | Br |
| 124 | F | CF$_3$ | Br | Br |
| 125 | CF$_3$ | CF$_3$ | Br | Br |
| 126 | H | CF$_2$Cl | Br | Br |
| 127 | Cl | CF$_2$Cl | Br | Br |
| 128 | Br | CF$_2$Cl | Br | Br |
| 129 | F | CF$_2$Cl | Br | Br |
| 130 | CF$_3$ | CF$_2$Cl | Br | Br |
| 131 | H | CF$_3$ | F | Br |
| 132 | Cl | CF$_3$ | F | Br |
| 133 | Br | CF$_3$ | F | Br |
| 134 | F | CF$_3$ | F | Br |
| 135 | CF$_3$ | CF$_3$ | F | Br |
| 136 | H | CF$_2$Cl | F | Br |
| 137 | Cl | CF$_2$Cl | F | Br |
| 138 | Br | CF$_2$Cl | F | Br |
| 139 | F | CF$_2$Cl | F | Br |
| 140 | CF$_3$ | CF$_2$Cl | F | Br |
| 141 | H | CF$_3$ | CF$_3$ | Br |
| 142 | Cl | CF$_3$ | CF$_3$ | Br |
| 143 | Br | CF$_3$ | CF$_3$ | Br |
| 144 | F | CF$_3$ | CF$_3$ | Br |
| 145 | CF$_3$ | CF$_3$ | CF$_3$ | Br |
| 146 | H | CF$_2$Cl | CF$_3$ | Br |
| 147 | Cl | CF$_2$Cl | CF$_3$ | Br |
| 148 | Br | CF$_2$Cl | CF$_3$ | Br |
| 149 | F | CF$_2$Cl | CF$_3$ | Br |
| 150 | CF$_3$ | CF$_2$Cl | CF$_3$ | Br |
| 151 | H | CF$_3$ | H | CF$_3$ |
| 152 | Cl | CF$_3$ | H | CF$_3$ |
| 153 | Br | CF$_3$ | H | CF$_3$ |
| 154 | F | CF$_3$ | H | CF$_3$ |
| 155 | CF$_3$ | CF$_3$ | H | CF$_3$ |
| 156 | H | CF$_2$Cl | H | CF$_3$ |
| 157 | Cl | CF$_2$Cl | H | CF$_3$ |
| 158 | Br | CF$_2$Cl | H | CF$_3$ |
| 159 | F | CF$_2$Cl | H | CF$_3$ |
| 160 | CF$_3$ | CF$_2$Cl | H | CF$_3$ |
| 161 | H | CF$_3$ | Cl | CF$_3$ |
| 162 | Cl | CF$_3$ | Cl | CF$_3$ |
| 163 | Br | CF$_3$ | Cl | CF$_3$ |
| 164 | F | CF$_3$ | Cl | CF$_3$ |
| 165 | CF$_3$ | CF$_3$ | Cl | CF$_3$ |
| 166 | H | CF$_2$Cl | Cl | CF$_3$ |
| 167 | Cl | CF$_2$Cl | Cl | CF$_3$ |
| 168 | Br | CF$_2$Cl | Cl | CF$_3$ |
| 169 | F | CF$_2$Cl | Cl | CF$_3$ |
| 170 | CF$_3$ | CF$_2$Cl | Cl | CF$_3$ |
| 171 | H | CF$_3$ | Br | CF$_3$ |
| 172 | Cl | CF$_3$ | Br | CF$_3$ |
| 173 | Br | CF$_3$ | Br | CF$_3$ |
| 174 | F | CF$_3$ | Br | CF$_3$ |
| 175 | CF$_3$ | CF$_3$ | Br | CF$_3$ |
| 176 | H | CF$_2$Cl | Br | CF$_3$ |
| 177 | Cl | CF$_2$Cl | Br | CF$_3$ |

TABLE P-continued

|     | $X_3$ | $R^3$ | $X_1$ | $R^5$ |
|-----|-------|-------|-------|-------|
| 178 | Br    | $CF_2Cl$ | Br | $CF_3$ |
| 179 | F     | $CF_2Cl$ | Br | $CF_3$ |
| 180 | $CF_3$ | $CF_2Cl$ | Br | $CF_3$ |
| 181 | H     | $CF_3$ | F  | $CF_3$ |
| 182 | Cl    | $CF_3$ | F  | $CF_3$ |
| 183 | Br    | $CF_3$ | F  | $CF_3$ |
| 184 | F     | $CF_3$ | F  | $CF_3$ |
| 185 | $CF_3$ | $CF_3$ | F  | $CF_3$ |
| 186 | H     | $CF_2Cl$ | F | $CF_3$ |
| 187 | Cl    | $CF_2Cl$ | F | $CF_3$ |
| 188 | Br    | $CF_2Cl$ | F | $CF_3$ |
| 189 | F     | $CF_2Cl$ | F | $CF_3$ |
| 190 | $CF_3$ | $CF_2Cl$ | F | $CF_3$ |
| 191 | H     | $CF_3$ | $CF_3$ | $CF_3$ |
| 192 | Cl    | $CF_3$ | $CF_3$ | $CF_3$ |
| 193 | Br    | $CF_3$ | $CF_3$ | $CF_3$ |
| 194 | F     | $CF_3$ | $CF_3$ | $CF_3$ |
| 195 | $CF_3$ | $CF_3$ | $CF_3$ | $CF_3$ |
| 196 | H     | $CF_2Cl$ | $CF_3$ | $CF_3$ |
| 197 | Cl    | $CF_2Cl$ | $CF_3$ | $CF_3$ |
| 198 | Br    | $CF_2Cl$ | $CF_3$ | $CF_3$ |
| 199 | F     | $CF_2Cl$ | $CF_3$ | $CF_3$ |
| 200 | $CF_3$ | $CF_2Cl$ | $CF_3$ | $CF_3$ |
| 201 | H     | $CF_3$ | H  | F |
| 202 | Cl    | $CF_3$ | H  | F |
| 203 | Br    | $CF_3$ | H  | F |
| 204 | F     | $CF_3$ | H  | F |
| 205 | $CF_3$ | $CF_3$ | H  | F |
| 206 | H     | $CF_2Cl$ | H | F |
| 207 | Cl    | $CF_2Cl$ | H | F |
| 208 | Br    | $CF_2Cl$ | H | F |
| 209 | F     | $CF_2Cl$ | H | F |
| 210 | $CF_3$ | $CF_2Cl$ | H | F |
| 211 | H     | $CF_3$ | Cl | F |
| 212 | Cl    | $CF_3$ | Cl | F |
| 213 | Br    | $CF_3$ | Cl | F |
| 214 | F     | $CF_3$ | Cl | F |
| 215 | $CF_3$ | $CF_3$ | Cl | F |
| 216 | H     | $CF_2Cl$ | Cl | F |
| 217 | Cl    | $CF_2Cl$ | Cl | F |
| 218 | Br    | $CF_2Cl$ | Cl | F |
| 219 | F     | $CF_2Cl$ | Cl | F |
| 220 | $CF_3$ | $CF_2Cl$ | Cl | F |
| 221 | H     | $CF_3$ | Br | F |
| 222 | Cl    | $CF_3$ | Br | F |
| 223 | Br    | $CF_3$ | Br | F |
| 224 | F     | $CF_3$ | Br | F |
| 225 | $CF_3$ | $CF_3$ | Br | F |
| 226 | H     | $CF_2Cl$ | Br | F |
| 227 | Cl    | $CF_2Cl$ | Br | F |
| 228 | Br    | $CF_2Cl$ | Br | F |
| 229 | F     | $CF_2Cl$ | Br | F |
| 230 | $CF_3$ | $CF_2Cl$ | Br | F |
| 231 | H     | $CF_3$ | F  | F |
| 232 | Cl    | $CF_3$ | F  | F |
| 233 | Br    | $CF_3$ | F  | F |
| 234 | F     | $CF_3$ | F  | F |
| 235 | $CF_3$ | $CF_3$ | F  | F |
| 236 | H     | $CF_2Cl$ | F | F |
| 237 | Cl    | $CF_2Cl$ | F | F |
| 238 | Br    | $CF_2Cl$ | F | F |
| 239 | F     | $CF_2Cl$ | F | F |
| 240 | $CF_3$ | $CF_2Cl$ | F | F |
| 241 | H     | $CF_3$ | $CF_3$ | F |
| 242 | Cl    | $CF_3$ | $CF_3$ | F |
| 243 | Br    | $CF_3$ | $CF_3$ | F |
| 244 | F     | $CF_3$ | $CF_3$ | F |
| 245 | $CF_3$ | $CF_3$ | $CF_3$ | F |
| 246 | H     | $CF_2Cl$ | $CF_3$ | F |
| 247 | Cl    | $CF_2Cl$ | $CF_3$ | F |
| 248 | Br    | $CF_2Cl$ | $CF_3$ | F |
| 249 | F     | $CF_2Cl$ | $CF_3$ | F |
| 250 | $CF_3$ | $CF_2Cl$ | $CF_3$ | F |

Table 1

Table 1 provides 250 compounds of formula (Ia) wherein $R^1$ is hydrogen, $X_2$ is N, and $X_3$, $R^3$, $X_1$, $R^5$ are as defined in Table P.

Table 2

Table 2 provides 250 compounds of formula (Ia) wherein $R^1$ is hydrogen, $X_2$ is CH, and $X_3$, $R^3$, $X_1$, $R^5$ are as defined in Table P.

Table 3

Table 3 provides 250 compounds of formula (Ia) wherein $R^1$ is hydrogen, $X_2$ is C—F, and $X_3$, $R^3$, $X_1$, $R^5$ are as defined in Table P.

Table 4

Table 4 provides 250 compounds of formula (Ia) wherein $R^1$ is hydrogen, $X_2$ is C—Br, and $X_3$, $R^3$, $X_1$, $R^5$ are as defined in Table P.

Table 5

Table 5 provides 250 compounds of formula (Ia) wherein $R^1$ is hydrogen, $X_2$ is C—Cl, and $X_3$, $R^3$, $X_1$, $R^5$ are as defined in Table P.

Table 6

Table 6 provides 250 compounds of formula (Ia) wherein $R^1$ is hydrogen, $X_2$ is C—$CF_3$, and $X_3$, $R^3$, $X_1$, $R^5$ are as defined in Table P.

Table 7

Table 7 provides 250 compounds of formula (Ia) wherein $R^1$ is $CH_2CN$, $X_2$ is N, and $X_3$, $R^3$, $X_1$, $R^5$ are as defined in Table P.

Table 8

Table 8 provides 250 compounds of formula (Ia) wherein $R^1$ is $CH_2CN$, $X_2$ is CH, and $X_3$, $R^3$, $X_1$, $R^5$ are as defined in Table P.

Table 9

Table 9 provides 250 compounds of formula (Ia) wherein $R^1$ is $CH_2CN$, $X_2$ is C—F, and $X_3$, $R^3$, $X_1$, $R^5$ are as defined in Table P.

Table 10

Table 10 provides 250 compounds of formula (Ia) wherein $R^1$ is $CH_2CN$, $X_2$ is C—Br, and $X_3$, $R^3$, $X_1$, $R^5$ are as defined in Table P.

Table 11

Table 11 provides 250 compounds of formula (Ia) wherein $R^1$ is $CH_2CN$, $X_2$ is C—Cl, and $X_3$, $R^3$, $X_1$, $R^5$ are as defined in Table P.

Table 12

Table 12 provides 250 compounds of formula (Ia) wherein $R^1$ is $CH_2CN$, $X_2$ is C—$CF_3$, and $X_3$, $R^3$, $X_1$, $R^5$ are as defined in Table P.

Table 13

Table 13 provides 250 compounds of formula (Ia) wherein $R^1$ is $CH_2OCH_3$, $X_2$ is N, and $X_3$, $R^3$, $X_1$, $R^5$ are as defined in Table P.

Table 14

Table 14 provides 250 compounds of formula (Ia) wherein $R^1$ is $CH_2OCH_3$, $X_2$ is CH, and $X_3$, $R^3$, $X_1$, $R^5$ are as defined in Table P.

Table 15

Table 15 provides 250 compounds of formula (Ia) wherein $R^1$ is $CH_2OCH_3$, $X_2$ is C—F, and $X_3$, $R^3$, $X_1$, $R^5$ are as defined in Table P.

Table 16

Table 16 provides 250 compounds of formula (Ia) wherein $R^1$ is $CH_2OCH_3$, $X_2$ is C—Br, and $X_3$, $R^3$, $X_1$, $R^5$ are as defined in Table P.

Table 17

Table 17 provides 250 compounds of formula (Ia) wherein $R^1$ is $CH_2OCH_3$, $X_2$ is C—Cl, and $X_3$, $R^3$, $X_1$, $R^5$ are as defined in Table P.

Table 18

Table 18 provides 250 compounds of formula (Ia) wherein $R^1$ is $CH_2OCH_3$, $X_2$ is C—$CF_3$, and $X_3$, $R^3$, $X_1$, $R^5$ are as defined in Table P.

Table 19

Table 19 provides 250 compounds of formula (Ia) wherein $R^1$ is $CH_2OCH_2CH_3$, $X_2$ is N, and $X_3$, $R^3$, $X_1$, $R^5$ are as defined in Table P.

Table 20

Table 20 provides 250 compounds of formula (Ia) wherein $R^1$ is $CH_2OCH_2CH_3$, $X_2$ is CH, and $X_3$, $R^3$, $X_1$, $R^5$ are as defined in Table P.

Table 21

Table 21 provides 250 compounds of formula (Ia) wherein $R^1$ is $CH_2OCH_2CH_3$, $X_2$ is C—F, and $X_3$, $R^3$, $X_1$, $R^5$ are as defined in Table P.

Table 22

Table 22 provides 250 compounds of formula (Ia) wherein $R^1$ is $CH_2OCH_2CH_3$, $X_2$ is C—Br, and $X_3$, $R^3$, $X_1$, $R^5$ are as defined in Table P.

Table 23

Table 23 provides 250 compounds of formula (Ia) wherein $R^1$ is $CH_2OCH_2CH_3$, $X_2$ is C—Cl, and $X_3$, $R^3$, $X_1$, $R^5$ are as defined in Table P.

Table 24

Table 24 provides 250 compounds of formula (Ia) wherein $R^1$ is $CH_2OCH_2CH_3$, $X_2$ is C—$CF_3$, and $X_3$, $R^3$, $X_1$, $R^5$ are as defined in Table P.

Table 25

Table 25 provides 250 compounds of formula (Ia) wherein $R^1$ is $C(O)OCH_3$, $X_2$ is N, and $X_3$, $R^3$, $X_1$, $R^5$ are as defined in Table P.

Table 26

Table 26 provides 250 compounds of formula (Ia) wherein $R^1$ is $C(O)OCH_3$, $X_2$ is CH, and $X_3$, $R^3$, $X_1$, $R^5$ are as defined in Table P.

Table 27

Table 27 provides 250 compounds of formula (Ia) wherein $R^1$ is $C(O)OCH_3$, $X_2$ is C—F, and $X_3$, $R^3$, $X_1$, $R^5$ are as defined in Table P.

Table 28

Table 28 provides 250 compounds of formula (Ia) wherein $R^1$ is $C(O)OCH_3$, $X_2$ is C—Br, and $X_3$, $R^3$, $X_1$, $R^5$ are as defined in Table P.

Table 29

Table 29 provides 250 compounds of formula (Ia) wherein $R^1$ is $C(O)OCH_3$, $X_2$ is C—Cl, and $X_3$, $R^3$, $X_1$, $R^5$ are as defined in Table P.

Table 30

Table 30 provides 250 compounds of formula (Ia) wherein $R^1$ is $C(O)OCH_3$, $X_2$ is C—$CF_3$, and $X_3$, $R^3$, $X_1$, $R^5$ are as defined in Table P.

Table 31

Table 31 provides 250 compounds of formula (Ia) wherein $R^1$ is $C(O)OCH_2CH_3$, $X_2$ is N, and $X_3$, $R^3$, $X_1$, $R^5$ are as defined in Table P.

Table 32

Table 32 provides 250 compounds of formula (Ia) wherein $R^1$ is $C(O)OCH_2CH_3$, $X_2$ is CH, and $X_3$, $R^3$, $X_1$, $R^5$ are as defined in Table P.

Table 33

Table 33 provides 250 compounds of formula (Ia) wherein $R^1$ is $C(O)OCH_2CH_3$, $X_2$ is C—F, and $X_3$, $R^3$, $X_1$, $R^5$ are as defined in Table P.

Table 34

Table 34 provides 250 compounds of formula (Ia) wherein $R^1$ is $C(O)OCH_2CH_3$, $X_2$ is C—Br, and $X_3$, $R^3$, $X_1$, $R^5$ are as defined in Table P.

Table 35

Table 35 provides 250 compounds of formula (Ia) wherein $R^1$ is $C(O)OCH_2CH_3$, $X_2$ is C—Cl, and $X_3$, $R^3$, $X_1$, $R^5$ are as defined in Table P.

Table 36

Table 36 provides 250 compounds of formula (Ia) wherein $R^1$ is $C(O)OCH_2CH_3$, $X_2$ is C—$CF_3$, and $X_3$, $R^3$, $X_1$, $R^5$ are as defined in Table P.

Table 37

Table 37 provides 250 compounds of formula (Ia) wherein $R^1$ is $CH_2OC(O)CH_3$, $X_2$ is N, and $X_3$, $R^3$, $X_1$, $R^5$ are as defined in Table P.

Table 38

Table 38 provides 250 compounds of formula (Ia) wherein $R^1$ is $CH_2OC(O)CH_3$, $X_2$ is CH, and $X_3$, $R^3$, $X_1$, $R^5$ are as defined in Table P.

Table 39

Table 39 provides 250 compounds of formula (Ia) wherein $R^1$ is $CH_2OC(O)CH_3$, $X_2$ is C—F, and $X_3$, $R^3$, $X_1$, $R^5$ are as defined in Table P.

Table 40

Table 40 provides 250 compounds of formula (Ia) wherein $R^1$ is $CH_2OC(O)CH_3$, $X_2$ is C—Br, and $X_3$, $R^3$, $X_1$, $R^5$ are as defined in Table P.

Table 41

Table 41 provides 250 compounds of formula (Ia) wherein $R^1$ is $CH_2OC(O)CH_3$, $X_2$ is C—Cl, and $X_3$, $R^3$, $X_1$, $R^5$ are as defined in Table P.

Table 42

Table 42 provides 250 compounds of formula (Ia) wherein $R^1$ is $CH_2OC(O)CH_3$, $X_2$ is C—$CF_3$, and $X_3$, $R^3$, $X_1$, $R^5$ are as defined in Table P.

Table 43

Table 43 provides 250 compounds of formula (Ia) wherein $R^1$ is $CH_2OC(O)CH(CH_3)_2$, $X_2$ is N, and $X_3$, $R^3$, $X_1$, $R^5$ are as defined in Table P.

Table 44

Table 44 provides 250 compounds of formula (Ia) wherein $R^1$ is $CH_2OC(O)CH(CH_3)_2$, $X_2$ is CH, and $X_3$, $R^3$, $X_1$, $R^5$ are as defined in Table P.

Table 45

Table 45 provides 250 compounds of formula (Ia) wherein $R^1$ is $CH_2OC(O)CH(CH_3)_2$, $X_2$ is C—F, and $X_3$, $R^3$, $X_1$, $R^5$ are as defined in Table P.

Table 46

Table 46 provides 250 compounds of formula (Ia) wherein $R^1$ is $CH_2OC(O)CH(CH_3)_2$, $X_2$ is C—Br, and $X_3$, $R^3$, $X_1$, $R^5$ are as defined in Table P.

Table 47

Table 47 provides 250 compounds of formula (Ia) wherein $R^1$ is $CH_2OC(O)CH(CH_3)_2$, $X_2$ is C—Cl, and $X_3$, $R^3$, $X_1$, $R^5$ are as defined in Table P.

Table 48

Table 48 provides 250 compounds of formula (Ia) wherein $R^1$ is $CH_2OC(O)CH(CH_3)_2$, $X_2$ is C—$CF_3$, and $X_3$, $R^3$, $X_1$, $R^5$ are as defined in Table P.

Table 49

Table 49 provides 250 compounds of formula (Ia) wherein $R^1$ is $CH_2OC(O)C(CH_3)_3$, $X_2$ is N, and $X_3$, $R^3$, $X_1$, $R^5$ are as defined in Table P.

Table 50

Table 50 provides 250 compounds of formula (Ia) wherein $R^1$ is $CH_2OC(O)C(CH_3)_3$, $X_2$ is CH, and $X_3$, $R^3$, $X_1$, $R^5$ are as defined in Table P.

Table 51

Table 51 provides 250 compounds of formula (Ia) wherein $R^1$ is $CH_2OC(O)C(CH_3)_3$, $X_2$ is C—F, and $X_3$, $R^3$, $X_1$, $R^5$ are as defined in Table P.

Table 52

Table 52 provides 250 compounds of formula (Ia) wherein $R^1$ is $CH_2OC(O)C(CH_3)_3$, $X_2$ is C—Br, and $X_3$, $R^3$, $X_1$, $R^5$ are as defined in Table P.

Table 53

Table 53 provides 250 compounds of formula (Ia) wherein $R^1$ is $CH_2OC(O)C(CH_3)_3$, $X_2$ is C—Cl, and $X_3$, $R^3$, $X_1$, $R^5$ are as defined in Table P.

Table 54

Table 54 provides 250 compounds of formula (Ia) wherein $R^1$ is $CH_2OC(O)C(CH_3)_3$, $X_2$ is C—$CF_3$, and $X_3$, $R^3$, $X_1$, $R^5$ are as defined in Table P.

Examples of compounds of formula (Int-Ia) made available are those where $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$ and $R^5$ correspond to substitutents $R^1$ and $R^5$ as defined in each of Tables 1 to 54 above in context of formula (Ia), So for example, Table 1 individualises a compound of formula (Int-I) wherein $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$ and $R^5$ are defined in Table 1; similarly, Table 2 individualises a compound of formula (Int-I) wherein $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$ and $R^5$ are defined in Table 2; and so on for Tables 3 to 54.

Examples of compounds of formula (Int-IIa) made available are those where $X^c$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(3,5-dichloro-4-fluoro-phenyl), CH=C($CF_3$)(3,4,5-trichloro-phenyl), $CH_2C(OH)(CF_3)$(3-chloro-5-trifluoromethyl-phenyl), $CH_2C(OH)(CF_3)$(3-bromo-5-trifluoromethyl-phenyl), $CH_2C(OH)(CF_3)$(3,5-dichloro-4-fluoro-phenyl) or $CH_2C(OH)(CF_3)$(3,4,5-trichloro-phenyl), $A^2$, $A^3$ and $A^4$ are each CH, n is 2, $A^1$ is $CR^5$, and $R^1$ and $R^5$ correspond to substitutents $R^1$ and $R^5$ as defined in each of Tables 1 to 54 above in context of formula (Ia), So for example, Table 1 individualises a compound of formula (Int-II) wherein $X^C$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(3,5-dichloro-4-fluoro-phenyl), CH=C($CF_3$)(3,4,5-trichloro-phenyl), $CH_2C(OH)(CF_3)$(3-chloro-5-trifluoromethyl-phenyl), $CH_2C(OH)(CF_3)$(3-bromo-5-trifluoromethyl-phenyl), $CH_2C(OH)(CF_3)$(3,5-dichloro-4-fluoro-phenyl) or $CH_2C(OH)(CF_3)$(3,4,5-trichloro-phenyl), $A^2$, $A^3$ and $A^4$ are each CH, n is 2, $A^1$ is $CR^5$, and wherein $R^1$ and $R^5$ are defined in Table 1; similarly, Table 2 individualises a compound of formula (Int-II) wherein $X^c$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(3,5-dichloro-4-fluoro-phenyl), CH=C($CF_3$)(3,4,5-trichloro-phenyl), $CH_2C(OH)(CF_3)$(3-chloro-5-trifluoromethyl-phenyl), $CH_2C(OH)(CF_3)$(3-bromo-5-trifluoromethyl-phenyl), $CH_2C(OH)(CF_3)$(3,5-dichloro-4-fluoro-phenyl) or $CH_2C(OH)(CF_3)$(3,4,5-trichloro-phenyl), $A^2$, $A^3$ and $A^4$ are each CH, n is 2, $A^1$ is $CR^5$, and wherein $R^1$ and $R^5$ are defined in Table 2; and so on for Tables 3 to 54.

Tables 55 to 108: Compounds of Formula (Ib)

The invention is further illustrated by making available the following individual compounds of formula (Ib) listed in Tables 55 to 108.

(Ib)

Each of Tables 55 to 108, which follow the Table P above, make available 250 compounds of the formula (Ib) in which $X_3$, $R^3$, $X_1$ and $R^5$ are the substituents defined in Table P and $R^1$ and $X_2$ are the substituents defined in the relevant Table 55 to 108. Thus Table 55 individualises 250 compounds of formula (Ib) wherein for each row of Table P, the $R^1$ and $X_2$ substituent are as defined in Table 55; similarly, Table 56 individualises 250 compounds of formula (Ib) wherein for each row of Table P, the $R^1$ and $X_2$ substituent are as defined in Table 56; and so on for Tables 57 to 108.

Table 55

Table 56 provides 250 compounds of formula (Ib) wherein $R^1$ is hydrogen, $X_2$ is N, and $X_3$, $R^3$, $X_1$, $R^5$ are as defined in Table P.

Table 56

Table 56 provides 250 compounds of formula (Ib) wherein $R^1$ is hydrogen, $X_2$ is CH, and $X_3$, $R^3$, $X_1$, $R^5$ are as defined in Table P.

Table 57

Table 57 provides 250 compounds of formula (Ib) wherein $R^1$ is hydrogen, $X_2$ is C—F, and $X_3$, $R^3$, $X_1$, $R^5$ are as defined in Table P.

Table 58

Table 58 provides 250 compounds of formula (Ib) wherein $R^1$ is hydrogen, $X_2$ is C—Br, and $X_3$, $R^3$, $X_1$, $R^5$ are as defined in Table P.

Table 59

Table 59 provides 250 compounds of formula (Ib) wherein $R^1$ is hydrogen, $X_2$ is C—Cl, and $X_3$, $R^3$, $X_1$, $R^5$ are as defined in Table P.

Table 60

Table 60 provides 250 compounds of formula (Ib) wherein $R^1$ is hydrogen, $X_2$ is C—$CF_3$, and $X_3$, $R^3$, $X_1$, $R^5$ are as defined in Table P.

Table 61

Table 61 provides 250 compounds of formula (Ib) wherein $R^1$ is $CH_2CN$, $X_2$ is N, and $X_3$, $R^3$, $X_1$, $R^5$ are as defined in Table P.

Table 62
Table 62 provides 250 compounds of formula (Ib) wherein $R^1$ is $CH_2CN$, $X_2$ is CH, and $X_3$, $R^3$, $X_1$, $R^5$ are as defined in Table P.
Table 63
Table 63 provides 250 compounds of formula (Ib) wherein $R^1$ is $CH_2CN$, $X_2$ is C—F, and $X_3$, $R^3$, $X_1$, $R^5$ are as defined in Table P.
Table 64
Table 64 provides 250 compounds of formula (Ib) wherein $R^1$ is $CH_2CN$, $X_2$ is C—Br, and $X_3$, $R^3$, $X_1$, $R^5$ are as defined in Table P.
Table 65
Table 65 provides 250 compounds of formula (Ib) wherein $R^1$ is $CH_2CN$, $X_2$ is C—Cl, and $X_3$, $R^3$, $X_1$, $R^5$ are as defined in Table P.
Table 66
Table 66 provides 250 compounds of formula (Ib) wherein $R^1$ is $CH_2CN$, $X_2$ is C—$CF_3$, and $X_3$, $R^3$, $X_1$, $R^5$ are as defined in Table P.
Table 67
Table 67 provides 250 compounds of formula (Ib) wherein $R^1$ is $CH_2OCH_3$, $X_2$ is N, and $X_3$, $R^3$, $X_1$, $R^5$ are as defined in Table P.
Table 68
Table 68 provides 250 compounds of formula (Ib) wherein $R^1$ is $CH_2OCH_3$, $X_2$ is CH, and $X_3$, $R^3$, $X_1$, $R^5$ are as defined in Table P.
Table 69
Table 69 provides 250 compounds of formula (Ib) wherein $R^1$ is $CH_2OCH_3$, $X_2$ is C—F, and $X_3$, $R^3$, $X_1$, $R^5$ are as defined in Table P.
Table 70
Table 70 provides 250 compounds of formula (Ib) wherein $R^1$ is $CH_2OCH_3$, $X_2$ is C—Br, and $X_3$, $R^3$, $X_1$, $R^5$ are as defined in Table P.
Table 71
Table 71 provides 250 compounds of formula (Ib) wherein $R^1$ is $CH_2OCH_3$, $X_2$ is C—Cl, and $X_3$, $R^3$, $X_1$, $R^5$ are as defined in Table P.
Table 72
Table 72 provides 250 compounds of formula (Ib) wherein $R^1$ is $CH_2OCH_3$, $X_2$ is C—$CF_3$, and $X_3$, $R^3$, $X_1$, $R^5$ are as defined in Table P.
Table 73
Table 73 provides 250 compounds of formula (Ib) wherein $R^1$ is $CH_2OCH_2CH_3$, $X_2$ is N, and $X_3$, $R^3$, $X_1$, $R^5$ are as defined in Table P.
Table 74
Table 74 provides 250 compounds of formula (Ib) wherein $R^1$ is $CH_2OCH_2CH_3$, $X_2$ is CH, and $X_3$, $R^3$, $X_1$, $R^5$ are as defined in Table P.
Table 75
Table 75 provides 250 compounds of formula (Ib) wherein $R^1$ is $CH_2OCH_2CH_3$, $X_2$ is C—F, and $X_3$, $R^3$, $X_1$, $R^5$ are as defined in Table P.
Table 76
Table 76 provides 250 compounds of formula (Ib) wherein $R^1$ is $CH_2OCH_2CH_3$, $X_2$ is C—Br, and $X_3$, $R^3$, $X_1$, $R^5$ are as defined in Table P.
Table 77
Table 77 provides 250 compounds of formula (Ib) wherein $R^1$ is $CH_2OCH_2CH_3$, $X_2$ is C—Cl, and $X_3$, $R^3$, $X_1$, $R^5$ are as defined in Table P.

Table 78
Table 78 provides 250 compounds of formula (Ib) wherein $R^1$ is $CH_2OCH_2CH_3$, $X_2$ is C—$CF_3$, and $X_3$, $R^3$, $X_1$, $R^5$ are as defined in Table P.
Table 79
Table 79 provides 250 compounds of formula (Ib) wherein $R^1$ is $C(O)OCH_3$, $X_2$ is N, and $X_3$, $R^3$, $X_1$, $R^5$ are as defined in Table P.
Table 80
Table 80 provides 250 compounds of formula (Ib) wherein $R^1$ is $C(O)OCH_3$, $X_2$ is CH, and $X_3$, $R^3$, $X_1$, $R^5$ are as defined in Table P.
Table 81
Table 81 provides 250 compounds of formula (Ib) wherein $R^1$ is $C(O)OCH_3$, $X_2$ is C—F, and $X_3$, $R^3$, $X_1$, $R^5$ are as defined in Table P.
Table 82
Table 82 provides 250 compounds of formula (Ib) wherein $R^1$ is $C(O)OCH_3$, $X_2$ is C—Br, and $X_3$, $R^3$, $X_1$, $R^5$ are as defined in Table P.
Table 83
Table 83 provides 250 compounds of formula (Ib) wherein $R^1$ is $C(O)OCH_3$, $X_2$ is C—Cl, and $X_3$, $R^3$, $X_1$, $R^5$ are as defined in Table P.
Table 84
Table 84 provides 250 compounds of formula (Ib) wherein $R^1$ is $C(O)OCH_3$, $X_2$ is C—$CF_3$, and $X_3$, $R^3$, $X_1$, $R^5$ are as defined in Table P.
Table 85
Table 85 provides 250 compounds of formula (Ib) wherein $R^1$ is $C(O)OCH_2CH_3$, $X_2$ is N, and $X_3$, $R^3$, $X_1$, $R^5$ are as defined in Table P.
Table 86
Table 86 provides 250 compounds of formula (Ib) wherein $R^1$ is $C(O)OCH_2CH_3$, $X_2$ is CH, and $X_3$, $R^3$, $X_1$, $R^5$ are as defined in Table P.
Table 87
Table 87 provides 250 compounds of formula (Ib) wherein $R^1$ is $C(O)OCH_2CH_3$, $X_2$ is C—F, and $X_3$, $R^3$, $X_1$, $R^5$ are as defined in Table P.
Table 88
Table 88 provides 250 compounds of formula (Ib) wherein $R^1$ is $C(O)OCH_2CH_3$, $X_2$ is C—Br, and $X_3$, $R^3$, $X_1$, $R^5$ are as defined in Table P.
Table 89
Table 89 provides 250 compounds of formula (Ib) wherein $R^1$ is $C(O)OCH_2CH_3$, $X_2$ is C—Cl, and $X_3$, $R^3$, $X_1$, $R^5$ are as defined in Table P.
Table 90
Table 90 provides 250 compounds of formula (Ib) wherein $R^1$ is $C(O)OCH_2CH_3$, $X_2$ is C—$CF_3$, and $X_3$, $R^3$, $X_1$, $R^5$ are as defined in Table P.
Table 91
Table 91 provides 250 compounds of formula (Ib) wherein $R^1$ is $CH_2OC(O)CH_3$, $X_2$ is N, and $X_3$, $R^3$, $X_1$, $R^5$ are as defined in Table P.
Table 92
Table 92 provides 250 compounds of formula (Ib) wherein $R^1$ is $CH_2OC(O)CH_3$, $X_2$ is CH, and $X_3$, $R^3$, $X_1$, $R^5$ are as defined in Table P.
Table 93
Table 93 provides 250 compounds of formula (Ib) wherein $R^1$ is $CH_2OC(O)CH_3$, $X_2$ is C—F, and $X_3$, $R^3$, $X_1$, $R^5$ are as defined in Table P.
Table 94
Table 94 provides 250 compounds of formula (Ib) wherein $R^1$ is $CH_2OC(O)CH_3$, $X_2$ is C—Br, and $X_3$, $R^3$, $X_1$, $R^5$ are as defined in Table P.

Table 95

Table 95 provides 250 compounds of formula (Ib) wherein $R^1$ is $CH_2OC(O)CH_3$, $X_2$ is C—Cl, and $X_3$, $R^3$, $X_1$, $R^5$ are as defined in Table P.

Table 96

Table 96 provides 250 compounds of formula (Ib) wherein $R^1$ is $CH_2OC(O)CH_3$, $X_2$ is C—$CF_3$, and $X_3$, $R^3$, $X_1$, $R^5$ are as defined in Table P.

Table 97

Table 97 provides 250 compounds of formula (Ib) wherein $R^1$ is $CH_2OC(O)CH(CH_3)_2$, $X_2$ is N, and $X_3$, $R^3$, $X_1$, $R^5$ are as defined in Table P.

Table 98

Table 98 provides 250 compounds of formula (Ib) wherein $R^1$ is $CH_2OC(O)CH(CH_3)_2$, $X_2$ is CH, and $X_3$, $R^3$, $X_1$, $R^5$ are as defined in Table P.

Table 99

Table 99 provides 250 compounds of formula (Ib) wherein $R^1$ is $CH_2OC(O)CH(CH_3)_2$, $X_2$ is C—F, and $X_3$, $R^3$, $X_1$, $R^5$ are as defined in Table P.

Table 100

Table 100 provides 250 compounds of formula (Ib) wherein $R^1$ is $CH_2OC(O)CH(CH_3)_2$, $X_2$ is C—Br, and $X_3$, $R^3$, $X_1$, $R^5$ are as defined in Table P.

Table 101

Table 101 provides 250 compounds of formula (Ib) wherein $R^1$ is $CH_2OC(O)CH(CH_3)_2$, $X_2$ is C—Cl, and $X_3$, $R^3$, $X_1$, $R^5$ are as defined in Table P.

Table 102

Table 102 provides 250 compounds of formula (Ib) wherein $R^1$ is $CH_2OC(O)CH(CH_3)_2$, $X_2$ is C—$CF_3$, and $X_3$, $R^3$, $X_1$, $R^5$ are as defined in Table P.

Table 103

Table 103 provides 250 compounds of formula (Ib) wherein $R^1$ is $CH_2OC(O)C(CH_3)_3$, $X_2$ is N, and $X_3$, $R^3$, $X_1$, $R^5$ are as defined in Table P.

Table 104

Table 104 provides 250 compounds of formula (Ib) wherein $R^1$ is $CH_2OC(O)C(CH_3)_3$, $X_2$ is CH, and $X_3$, $R^3$, $X_1$, $R^5$ are as defined in Table P.

Table 105

Table 105 provides 250 compounds of formula (Ib) wherein $R^1$ is $CH_2OC(O)C(CH_3)_3$, $X_2$ is C—F, and $X_3$, $R^3$, $X_1$, $R^5$ are as defined in Table P.

Table 106

Table 106 provides 250 compounds of formula (Ib) wherein $R^1$ is $CH_2OC(O)C(CH_3)_3$, $X_2$ is C—Br, and $X_3$, $R^3$, $X_1$, $R^5$ are as defined in Table P.

Table 107

Table 107 provides 250 compounds of formula (Ib) wherein $R^1$ is $CH_2OC(O)C(CH_3)_3$, $X_2$ is C—Cl, and $X_3$, $R^3$, $X_1$, $R^5$ are as defined in Table P.

Table 108

Table 108 provides 250 compounds of formula (Ib) wherein $R^1$ is $CH_2OC(O)C(CH_3)_3$, $X_2$ is C—$CF_3$, and $X_3$, $R^3$, $X_1$, $R^5$ are as defined in Table P.

Tables 109 to 162: Compounds of Formula (Ic)

The invention is further illustrated by making available the following individual compounds of formula (Ic) listed in Tables 109 to 162.

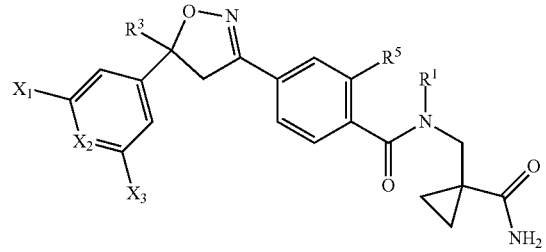

(Ic)

Each of Tables 109 to 162, which follow the Table P above, make available 250 compounds of the formula (Ic) in which $X_3$, $R^3$, $X_1$ and $R^5$ are the substituents defined in Table P and $R^1$ and $X_2$ are the substituents defined in the relevant Tables 109 to 162. Thus Table 109 individualises 250 compounds of formula (Ic) wherein for each row of Table P, the $R^1$ and $X_2$ substituents are as defined in Table 109; similarly, Table 110 individualises 250 compounds of formula (Ic) wherein for each row of Table P, the $R^1$ and $X_2$ substituent is as defined in Table 110; and so on for Tables 111 to 162.

Table 109

Table 109 provides 250 compounds of formula (Ic) wherein $R^1$ is hydrogen, $X_2$ is N, and $X_3$, $R^3$, $X_1$, $R^5$ are as defined in Table P.

Table 110

Table 110 provides 250 compounds of formula (Ic) wherein $R^1$ is hydrogen, $X_2$ is CH, and $X_3$, $R^3$, $X_1$, $R^5$ are as defined in Table P.

Table 111

Table 111 provides 250 compounds of formula (Ic) wherein $R^1$ is hydrogen, $X_2$ is C—F, and $X_3$, $R^3$, $X_1$, $R^5$ are as defined in Table P.

Table 112

Table 112 provides 250 compounds of formula (Ic) wherein $R^1$ is hydrogen, $X_2$ is C—Br, and $X_3$, $R^3$, $X_1$, $R^5$ are as defined in Table P.

Table 113

Table 113 provides 250 compounds of formula (Ic) wherein $R^1$ is hydrogen, $X_2$ is C—Cl, and $X_3$, $R^3$, $X_1$, $R^5$ are as defined in Table P.

Table 114

Table 114 provides 250 compounds of formula (Ic) wherein $R^1$ is hydrogen, $X_2$ is C—$CF_3$, and $X_3$, $R^3$, $X_1$, $R^5$ are as defined in Table P.

Table 115

Table 115 provides 250 compounds of formula (Ic) wherein $R^1$ is $CH_2CN$, $X_2$ is N, and $X_3$, $R^3$, $X_1$, $R^5$ are as defined in Table P.

Table 116

Table 116 provides 250 compounds of formula (Ic) wherein $R^1$ is $CH_2CN$, $X_2$ is CH, and $X_3$, $R^3$, $X_1$, $R^5$ are as defined in Table P.

Table 117

Table 117 provides 250 compounds of formula (Ic) wherein $R^1$ is $CH_2CN$, $X_2$ is C—F, and $X_3$, $R^3$, $X_1$, $R^5$ are as defined in Table P.

Table 118

Table 118 provides 250 compounds of formula (Ic) wherein $R^1$ is $CH_2CN$, $X_2$ is C—Br, and $X_3$, $R^3$, $X_1$, $R^5$ are as defined in Table P.

Table 119

Table 119 provides 250 compounds of formula (Ic) wherein $R^1$ is $CH_2CN$, $X_2$ is C—Cl, and $X_3$, $R^3$, $X_1$, $R^5$ are as defined in Table P.

Table 120

Table 120 provides 250 compounds of formula (Ic) wherein $R^1$ is $CH_2CN$, $X_2$ is C—$CF_3$, and $X_3$, $R^3$, $X_1$, $R^5$ are as defined in Table P.

Table 121

Table 121 provides 250 compounds of formula (Ic) wherein $R^1$ is $CH_2OCH_3$, $X_2$ is N, and $X_3$, $R^3$, $X_1$, $R^5$ are as defined in Table P.

Table 122

Table 122 provides 250 compounds of formula (Ic) wherein $R^1$ is $CH_2OCH_3$, $X_2$ is CH, and $X_3$, $R^3$, $X_1$, $R^5$ are as defined in Table P.

Table 123

Table 123 provides 250 compounds of formula (Ic) wherein $R^1$ is $CH_2OCH_3$, $X_2$ is C—F, and $X_3$, $R^3$, $X_1$, $R^5$ are as defined in Table P.

Table 124

Table 124 provides 250 compounds of formula (Ic) wherein $R^1$ is $CH_2OCH_3$, $X_2$ is C—Br, and $X_3$, $R^3$, $X_1$, $R^5$ are as defined in Table P.

Table 125

Table 125 provides 250 compounds of formula (Ic) wherein $R^1$ is $CH_2OCH_3$, $X_2$ is C—Cl, and $X_3$, $R^3$, $X_1$, $R^5$ are as defined in Table P.

Table 126

Table 126 provides 250 compounds of formula (Ic) wherein $R^1$ is $CH_2OCH_3$, $X_2$ is C—$CF_3$, and $X_3$, $R^3$, $X_1$, $R^5$ are as defined in Table P.

Table 127

Table 127 provides 250 compounds of formula (Ic) wherein $R^1$ is $CH_2OCH_2CH_3$, $X_2$ is N, and $X_3$, $R^3$, $X_1$, $R^5$ are as defined in Table P.

Table 128

Table 128 provides 250 compounds of formula (Ic) wherein $R^1$ is $CH_2OCH_2CH_3$, $X_2$ is CH, and $X_3$, $R^3$, $X_1$, $R^5$ are as defined in Table P.

Table 129

Table 129 provides 250 compounds of formula (Ic) wherein $R^1$ is $CH_2OCH_2CH_3$, $X_2$ is C—F, and $X_3$, $R^3$, $X_1$, $R^5$ are as defined in Table P.

Table 130

Table 130 provides 250 compounds of formula (Ic) wherein $R^1$ is $CH_2OCH_2CH_3$, $X_2$ is C—Br, and $X_3$, $R^3$, $X_1$, $R^5$ are as defined in Table P.

Table 131

Table 131 provides 250 compounds of formula (Ic) wherein $R^1$ is $CH_2OCH_2CH_3$, $X_2$ is C—Cl, and $X_3$, $R^3$, $X_1$, $R^5$ are as defined in Table P.

Table 132

Table 132 provides 250 compounds of formula (Ic) wherein $R^1$ is $CH_2OCH_2CH_3$, $X_2$ is C—$CF_3$, and $X_3$, $R^3$, $X_1$, $R^5$ are as defined in Table P.

Table 133

Table 133 provides 250 compounds of formula (Ic) wherein $R^1$ is $C(O)OCH_3$, $X_2$ is N, and $X_3$, $R^3$, $X_1$, $R^5$ are as defined in Table P.

Table 134

Table 134 provides 250 compounds of formula (Ic) wherein $R^1$ is $C(O)OCH_3$, $X_2$ is CH, and $X_3$, $R^3$, $X_1$, $R^5$ are as defined in Table P.

Table 135

Table 135 provides 250 compounds of formula (Ic) wherein $R^1$ is $C(O)OCH_3$, $X_2$ is C—F, and $X_3$, $R^3$, $X_1$, $R^5$ are as defined in Table P.

Table 136

Table 136 provides 250 compounds of formula (Ic) wherein $R^1$ is $C(O)OCH_3$, $X_2$ is C—Br, and $X_3$, $R^3$, $X_1$, $R^5$ are as defined in Table P.

Table 137

Table 137 provides 250 compounds of formula (Ic) wherein $R^1$ is $C(O)OCH_3$, $X_2$ is C—Cl, and $X_3$, $R^3$, $X_1$, $R^5$ are as defined in Table P.

Table 138

Table 138 provides 250 compounds of formula (Ic) wherein $R^1$ is $C(O)OCH_3$, $X_2$ is C—$CF_3$, and $X_3$, $R^3$, $X_1$, $R^5$ are as defined in Table P.

Table 139

Table 139 provides 250 compounds of formula (Ic) wherein $R^1$ is $C(O)OCH_2CH_3$, $X_2$ is N, and $X_3$, $R^3$, $X_1$, $R^5$ are as defined in Table P.

Table 140

Table 140 provides 250 compounds of formula (Ic) wherein $R^1$ is $C(O)OCH_2CH_3$, $X_2$ is CH, and $X_3$, $R^3$, $X_1$, $R^5$ are as defined in Table P.

Table 141

Table 141 provides 250 compounds of formula (Ic) wherein $R^1$ is $C(O)OCH_2CH_3$, $X_2$ is C—F, and $X_3$, $R^3$, $X_1$, $R^5$ are as defined in Table P.

Table 142

Table 142 provides 250 compounds of formula (Ic) wherein $R^1$ is $C(O)OCH_2CH_3$, $X_2$ is C—Br, and $X_3$, $R^3$, $X_1$, $R^5$ are as defined in Table P.

Table 143

Table 143 provides 250 compounds of formula (Ic) wherein $R^1$ is $C(O)OCH_2CH_3$, $X_2$ is C—Cl, and $X_3$, $R^3$, $X_1$, $R^5$ are as defined in Table P.

Table 144

Table 144 provides 250 compounds of formula (Ic) wherein $R^1$ is $C(O)OCH_2CH_3$, $X_2$ is C—$CF_3$, and $X_3$, $R^3$, $X_1$, $R^5$ are as defined in Table P.

Table 145

Table 145 provides 250 compounds of formula (Ic) wherein $R^1$ is $CH_2OC(O)CH_3$, $X_2$ is N, and $X_3$, $R^3$, $X_1$, $R^5$ are as defined in Table P.

Table 146

Table 146 provides 250 compounds of formula (Ic) wherein $R^1$ is $CH_2OC(O)CH_3$, $X_2$ is CH, and $X_3$, $R^3$, $X_1$, $R^5$ are as defined in Table P.

Table 147

Table 147 provides 250 compounds of formula (Ic) wherein $R^1$ is $CH_2OC(O)CH_3$, $X_2$ is C—F, and $X_3$, $R^3$, $X_1$, $R^5$ are as defined in Table P.

Table 148

Table 148 provides 250 compounds of formula (Ic) wherein $R^1$ is $CH_2OC(O)CH_3$, $X_2$ is C—Br, and $X_3$, $R^3$, $X_1$, $R^5$ are as defined in Table P.

Table 149

Table 149 provides 250 compounds of formula (Ic) wherein $R^1$ is $CH_2OC(O)CH_3$, $X_2$ is C—Cl, and $X_3$, $R^3$, $X_1$, $R^5$ are as defined in Table P.

Table 150

Table 150 provides 250 compounds of formula (Ic) wherein $R^1$ is $CH_2OC(O)CH_3$, $X_2$ is C—$CF_3$, and $X_3$, $R^3$, $X_1$, $R^5$ are as defined in Table P.

Table 151

Table 151 provides 250 compounds of formula (Ic) wherein $R^1$ is $CH_2OC(O)CH(CH_3)_2$, $X_2$ is N, and $X_3$, $R^3$, $X_1$, $R^5$ are as defined in Table P.

Table 152

Table 152 provides 250 compounds of formula (Ic) wherein $R^1$ is $CH_2OC(O)CH(CH_3)_2$, $X_2$ is CH, and $X_3$, $R^3$, $X_1$, $R^5$ are as defined in Table P.

Table 153

Table 153 provides 250 compounds of formula (Ic) wherein $R^1$ is $CH_2OC(O)CH(CH_3)_2$, $X_2$ is C—F, and $X_3$, $R^3$, $X_1$, $R^5$ are as defined in Table P.

Table 154

Table 154 provides 250 compounds of formula (Ic) wherein $R^1$ is $CH_2OC(O)CH(CH_3)_2$, $X_2$ is C—Br, and $X_3$, $R^3$, $X_1$, $R^5$ are as defined in Table P.

Table 155

Table 155 provides 250 compounds of formula (Ic) wherein $R^1$ is $CH_2OC(O)CH(CH_3)_2$, $X_2$ is C—Cl, and $X_3$, $R^3$, $X_1$, $R^5$ are as defined in Table P.

Table 156

Table 156 provides 250 compounds of formula (Ic) wherein $R^1$ is $CH_2OC(O)CH(CH_3)_2$, $X_2$ is C—$CF_3$, and $X_3$, $R^3$, $X_1$, $R^5$ are as defined in Table P.

Table 157

Table 157 provides 250 compounds of formula (Ic) wherein $R^1$ is $CH_2OC(O)C(CH_3)_3$, $X_2$ is N, and $X_3$, $R^3$, $X_1$, $R^5$ are as defined in Table P.

Table 158

Table 158 provides 250 compounds of formula (Ic) wherein $R^1$ is $CH_2OC(O)C(CH_3)_3$, $X_2$ is CH, and $X_3$, $R^3$, $X_1$, $R^5$ are as defined in Table P.

Table 159

Table 159 provides 250 compounds of formula (Ic) wherein $R^1$ is $CH_2OC(O)C(CH_3)_3$, $X_2$ is C—F, and $X_3$, $R^3$, $X_1$, $R^5$ are as defined in Table P.

Table 160

Table 160 provides 250 compounds of formula (Ic) wherein $R^1$ is $CH_2OC(O)C(CH_3)_3$, $X_2$ is C—Br, and $X_3$, $R^3$, $X_1$, $R^5$ are as defined in Table P.

Table 161

Table 161 provides 250 compounds of formula (Ic) wherein $R^1$ is $CH_2OC(O)C(CH_3)_3$, $X_2$ is C—Cl, and $X_3$, $R^3$, $X_1$, $R^5$ are as defined in Table P.

Table 162

Table 162 provides 250 compounds of formula (Ic) wherein $R^1$ is $CH_2OC(O)C(CH_3)_3$, $X_2$ is C—$CF_3$, and $X_3$, $R^3$, $X_1$, $R^5$ are as defined in Table P.

The invention is further illustrated by making available the following individual compounds of formula (Id) listed in Tables B-1 to B-270

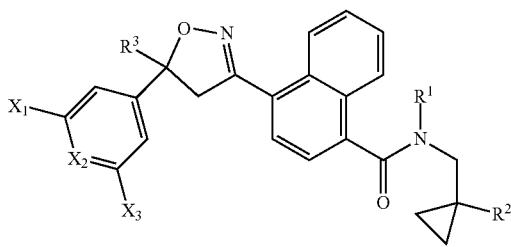

(Id)

TABLE P1

Substituent definitions of $R^2$, $R^3$, $X_3$ and $R^1$:

| | $R^3$ | $X_3$ | $R^2$ | $R^1$ |
|---|---|---|---|---|
| 1 | $CF_3$ | H | CN | H |
| 2 | $CF_3$ | Cl | CN | H |
| 3 | $CF_3$ | Br | CN | H |
| 4 | $CF_3$ | F | CN | H |
| 5 | $CF_3$ | $CF_3$ | CN | H |
| 6 | $CF_2Cl$ | H | CN | H |
| 7 | $CF_2Cl$ | Cl | CN | H |
| 8 | $CF_2Cl$ | Br | CN | H |
| 9 | $CF_2Cl$ | F | CN | H |
| 10 | $CF_2Cl$ | $CF_3$ | CN | H |
| 11 | $CF_3$ | H | $C(O)NH_2$ | H |
| 12 | $CF_3$ | Cl | $C(O)NH_2$ | H |
| 13 | $CF_3$ | Br | $C(O)NH_2$ | H |
| 14 | $CF_3$ | F | $C(O)NH_2$ | H |
| 15 | $CF_3$ | $CF_3$ | $C(O)NH_2$ | H |
| 16 | $CF_2Cl$ | H | $C(O)NH_2$ | H |
| 17 | $CF_2Cl$ | Cl | $C(O)NH_2$ | H |
| 18 | $CF_2Cl$ | Br | $C(O)NH_2$ | H |
| 19 | $CF_2Cl$ | F | $C(O)NH_2$ | H |
| 20 | $CF_2Cl$ | $CF_3$ | $C(O)NH_2$ | H |
| 21 | $CF_3$ | H | $C(S)NH_2$ | H |
| 22 | $CF_3$ | Cl | $C(S)NH_2$ | H |
| 23 | $CF_3$ | Br | $C(S)NH_2$ | H |
| 24 | $CF_3$ | F | $C(S)NH_2$ | H |
| 25 | $CF_3$ | $CF_3$ | $C(S)NH_2$ | H |
| 26 | $CF_2Cl$ | H | $C(S)NH_2$ | H |
| 27 | $CF_2Cl$ | Cl | $C(S)NH_2$ | H |
| 28 | $CF_2Cl$ | Br | $C(S)NH_2$ | H |
| 29 | $CF_2Cl$ | F | $C(S)NH_2$ | H |
| 30 | $CF_2Cl$ | $CF_3$ | $C(S)NH_2$ | H |
| 31 | $CF_3$ | H | CN | $CH_2CN$ |
| 32 | $CF_3$ | Cl | CN | $CH_2CN$ |
| 33 | $CF_3$ | Br | CN | $CH_2CN$ |
| 34 | $CF_3$ | F | CN | $CH_2CN$ |
| 35 | $CF_3$ | $CF_3$ | CN | $CH_2CN$ |
| 36 | $CF_2Cl$ | H | CN | $CH_2CN$ |
| 37 | $CF_2Cl$ | Cl | CN | $CH_2CN$ |
| 38 | $CF_2Cl$ | Br | CN | $CH_2CN$ |
| 39 | $CF_2Cl$ | F | CN | $CH_2CN$ |
| 40 | $CF_2Cl$ | $CF_3$ | CN | $CH_2CN$ |
| 41 | $CF_3$ | H | $C(O)NH_2$ | $CH_2CN$ |
| 42 | $CF_3$ | Cl | $C(O)NH_2$ | $CH_2CN$ |
| 43 | $CF_3$ | Br | $C(O)NH_2$ | $CH_2CN$ |
| 44 | $CF_3$ | F | $C(O)NH_2$ | $CH_2CN$ |
| 45 | $CF_3$ | $CF_3$ | $C(O)NH_2$ | $CH_2CN$ |
| 46 | $CF_2Cl$ | H | $C(O)NH_2$ | $CH_2CN$ |
| 47 | $CF_2Cl$ | Cl | $C(O)NH_2$ | $CH_2CN$ |
| 48 | $CF_2Cl$ | Br | $C(O)NH_2$ | $CH_2CN$ |
| 49 | $CF_2Cl$ | F | $C(O)NH_2$ | $CH_2CN$ |
| 50 | $CF_2Cl$ | $CF_3$ | $C(O)NH_2$ | $CH_2CN$ |
| 51 | $CF_3$ | H | $C(S)NH_2$ | $CH_2CN$ |
| 52 | $CF_3$ | Cl | $C(S)NH_2$ | $CH_2CN$ |
| 53 | $CF_3$ | Br | $C(S)NH_2$ | $CH_2CN$ |
| 54 | $CF_3$ | F | $C(S)NH_2$ | $CH_2CN$ |
| 55 | $CF_3$ | $CF_3$ | $C(S)NH_2$ | $CH_2CN$ |
| 56 | $CF_2Cl$ | H | $C(S)NH_2$ | $CH_2CN$ |
| 57 | $CF_2Cl$ | Cl | $C(S)NH_2$ | $CH_2CN$ |
| 58 | $CF_2Cl$ | Br | $C(S)NH_2$ | $CH_2CN$ |
| 59 | $CF_2Cl$ | F | $C(S)NH_2$ | $CH_2CN$ |
| 60 | $CF_2Cl$ | $CF_3$ | $C(S)NH_2$ | $CH_2CN$ |
| 61 | $CF_3$ | H | CN | $CH_2OCH_3$ |
| 62 | $CF_3$ | Cl | CN | $CH_2OCH_3$ |
| 63 | $CF_3$ | Br | CN | $CH_2OCH_3$ |
| 64 | $CF_3$ | F | CN | $CH_2OCH_3$ |
| 65 | $CF_3$ | $CF_3$ | CN | $CH_2OCH_3$ |
| 66 | $CF_2Cl$ | H | CN | $CH_2OCH_3$ |
| 67 | $CF_2Cl$ | Cl | CN | $CH_2OCH_3$ |
| 68 | $CF_2Cl$ | Br | CN | $CH_2OCH_3$ |
| 69 | $CF_2Cl$ | F | CN | $CH_2OCH_3$ |
| 70 | $CF_2Cl$ | $CF_3$ | CN | $CH_2OCH_3$ |
| 71 | $CF_3$ | H | $C(O)NH_2$ | $CH_2OCH_3$ |
| 72 | $CF_3$ | Cl | $C(O)NH_2$ | $CH_2OCH_3$ |
| 73 | $CF_3$ | Br | $C(O)NH_2$ | $CH_2OCH_3$ |
| 74 | $CF_3$ | F | $C(O)NH_2$ | $CH_2OCH_3$ |
| 75 | $CF_3$ | $CF_3$ | $C(O)NH_2$ | $CH_2OCH_3$ |
| 76 | $CF_2Cl$ | H | $C(O)NH_2$ | $CH_2OCH_3$ |

TABLE P1-continued

Substituent definitions of $R^2$, $R^3$, $X_3$ and $R^1$:

| | $R^3$ | $X_3$ | $R^2$ | $R^1$ |
|---|---|---|---|---|
| 77 | $CF_2Cl$ | Cl | $C(O)NH_2$ | $CH_2OCH_3$ |
| 78 | $CF_2Cl$ | Br | $C(O)NH_2$ | $CH_2OCH_3$ |
| 79 | $CF_2Cl$ | F | $C(O)NH_2$ | $CH_2OCH_3$ |
| 80 | $CF_2Cl$ | $CF_3$ | $C(O)NH_2$ | $CH_2OCH_3$ |
| 81 | $CF_3$ | H | $C(S)NH_2$ | $CH_2OCH_3$ |
| 82 | $CF_3$ | Cl | $C(S)NH_2$ | $CH_2OCH_3$ |
| 83 | $CF_3$ | Br | $C(S)NH_2$ | $CH_2OCH_3$ |
| 84 | $CF_3$ | F | $C(S)NH_2$ | $CH_2OCH_3$ |
| 85 | $CF_3$ | $CF_3$ | $C(S)NH_2$ | $CH_2OCH_3$ |
| 86 | $CF_2Cl$ | H | $C(S)NH_2$ | $CH_2OCH_3$ |
| 87 | $CF_2Cl$ | Cl | $C(S)NH_2$ | $CH_2OCH_3$ |
| 88 | $CF_2Cl$ | Br | $C(S)NH_2$ | $CH_2OCH_3$ |
| 89 | $CF_2Cl$ | F | $C(S)NH_2$ | $CH_2OCH_3$ |
| 90 | $CF_2Cl$ | $CF_3$ | $C(S)NH_2$ | $CH_2OCH_3$ |
| 91 | $CF_3$ | H | CN | $CH_2OCH_2CH_3$ |
| 92 | $CF_3$ | Cl | CN | $CH_2OCH_2CH_3$ |
| 93 | $CF_3$ | Br | CN | $CH_2OCH_2CH_3$ |
| 94 | $CF_3$ | F | CN | $CH_2OCH_2CH_3$ |
| 95 | $CF_3$ | $CF_3$ | CN | $CH_2OCH_2CH_3$ |
| 96 | $CF_2Cl$ | H | CN | $CH_2OCH_2CH_3$ |
| 97 | $CF_2Cl$ | Cl | CN | $CH_2OCH_2CH_3$ |
| 98 | $CF_2Cl$ | Br | CN | $CH_2OCH_2CH_3$ |
| 99 | $CF_2Cl$ | F | CN | $CH_2OCH_2CH_3$ |
| 100 | $CF_2Cl$ | $CF_3$ | CN | $CH_2OCH_2CH_3$ |
| 101 | $CF_3$ | H | $C(O)NH_2$ | $CH_2OCH_2CH_3$ |
| 10 | $CF_3$ | Cl | $C(O)NH_2$ | $CH_2OCH_2CH_3$ |
| 103 | $CF_3$ | Br | $C(O)NH_2$ | $CH_2OCH_2CH_3$ |
| 104 | $CF_3$ | F | $C(O)NH_2$ | $CH_2OCH_2CH_3$ |
| 105 | $CF_3$ | $CF_3$ | $C(O)NH_2$ | $CH_2OCH_2CH_3$ |
| 106 | $CF_2Cl$ | H | $C(O)NH_2$ | $CH_2OCH_2CH_3$ |
| 107 | $CF_2Cl$ | Cl | $C(O)NH_2$ | $CH_2OCH_2CH_3$ |
| 108 | $CF_2Cl$ | Br | $C(O)NH_2$ | $CH_2OCH_2CH_3$ |
| 109 | $CF_2Cl$ | F | $C(O)NH_2$ | $CH_2OCH_2CH_3$ |
| 110 | $CF_2Cl$ | $CF_3$ | $C(O)NH_2$ | $CH_2OCH_2CH_3$ |
| 111 | $CF_3$ | H | $C(S)NH_2$ | $CH_2OCH_2CH_3$ |
| 112 | $CF_3$ | Cl | $C(S)NH_2$ | $CH_2OCH_2CH_3$ |
| 113 | $CF_3$ | Br | $C(S)NH_2$ | $CH_2OCH_2CH_3$ |
| 114 | $CF_3$ | F | $C(S)NH_2$ | $CH_2OCH_2CH_3$ |
| 115 | $CF_3$ | $CF_3$ | $C(S)NH_2$ | $CH_2OCH_2CH_3$ |
| 116 | $CF_2Cl$ | H | $C(S)NH_2$ | $CH_2OCH_2CH_3$ |
| 117 | $CF_2Cl$ | Cl | $C(S)NH_2$ | $CH_2OCH_2CH_3$ |
| 118 | $CF_2Cl$ | Br | $C(S)NH_2$ | $CH_2OCH_2CH_3$ |
| 119 | $CF_2Cl$ | F | $C(S)NH_2$ | $CH_2OCH_2CH_3$ |
| 120 | $CF_2Cl$ | $CF_3$ | $C(S)NH_2$ | $CH_2OCH_2CH_3$ |
| 121 | $CF_3$ | H | CN | $C(O)OCH_3$ |
| 122 | $CF_3$ | Cl | CN | $C(O)OCH_3$ |
| 123 | $CF_3$ | Br | CN | $C(O)OCH_3$ |
| 124 | $CF_3$ | F | CN | $C(O)OCH_3$ |
| 125 | $CF_3$ | $CF_3$ | CN | $C(O)OCH_3$ |
| 126 | $CF_2Cl$ | H | CN | $C(O)OCH_3$ |
| 127 | $CF_2Cl$ | Cl | CN | $C(O)OCH_3$ |
| 128 | $CF_2Cl$ | Br | CN | $C(O)OCH_3$ |
| 129 | $CF_2Cl$ | F | CN | $C(O)OCH_3$ |
| 130 | $CF_2Cl$ | $CF_3$ | CN | $C(O)OCH_3$ |
| 131 | $CF_3$ | H | $C(O)NH_2$ | $C(O)OCH_3$ |
| 132 | $CF_3$ | Cl | $C(O)NH_2$ | $C(O)OCH_3$ |
| 133 | $CF_3$ | Br | $C(O)NH_2$ | $C(O)OCH_3$ |
| 134 | $CF_3$ | F | $C(O)NH_2$ | $C(O)OCH_3$ |
| 135 | $CF_3$ | $CF_3$ | $C(O)NH_2$ | $C(O)OCH_3$ |
| 136 | $CF_2Cl$ | H | $C(O)NH_2$ | $C(O)OCH_3$ |
| 137 | $CF_2Cl$ | Cl | $C(O)NH_2$ | $C(O)OCH_3$ |
| 138 | $CF_2Cl$ | Br | $C(O)NH_2$ | $C(O)OCH_3$ |
| 139 | $CF_2Cl$ | F | $C(O)NH_2$ | $C(O)OCH_3$ |
| 140 | $CF_2Cl$ | $CF_3$ | $C(O)NH_2$ | $C(O)OCH_3$ |
| 141 | $CF_3$ | H | $C(S)NH_2$ | $C(O)OCH_3$ |
| 142 | $CF_3$ | Cl | $C(S)NH_2$ | $C(O)OCH_3$ |
| 143 | $CF_3$ | Br | $C(S)NH_2$ | $C(O)OCH_3$ |
| 144 | $CF_3$ | F | $C(S)NH_2$ | $C(O)OCH_3$ |
| 145 | $CF_3$ | $CF_3$ | $C(S)NH_2$ | $C(O)OCH_3$ |
| 146 | $CF_2Cl$ | H | $C(S)NH_2$ | $C(O)OCH_3$ |
| 147 | $CF_2Cl$ | Cl | $C(S)NH_2$ | $C(O)OCH_3$ |
| 148 | $CF_2Cl$ | Br | $C(S)NH_2$ | $C(O)OCH_3$ |
| 149 | $CF_2Cl$ | F | $C(S)NH_2$ | $C(O)OCH_3$ |
| 150 | $CF_2Cl$ | $CF_3$ | $C(S)NH_2$ | $C(O)OCH_3$ |
| 151 | $CF_3$ | H | CN | $C(O)OCH_2CH_3$ |
| 152 | $CF_3$ | Cl | CN | $C(O)OCH_2CH_3$ |
| 153 | $CF_3$ | Br | CN | $C(O)OCH_2CH_3$ |
| 154 | $CF_3$ | F | CN | $C(O)OCH_2CH_3$ |
| 155 | $CF_3$ | $CF_3$ | CN | $C(O)OCH_2CH_3$ |
| 156 | $CF_2Cl$ | H | CN | $C(O)OCH_2CH_3$ |
| 157 | $CF_2Cl$ | Cl | CN | $C(O)OCH_2CH_3$ |
| 158 | $CF_2Cl$ | Br | CN | $C(O)OCH_2CH_3$ |
| 159 | $CF_2Cl$ | F | CN | $C(O)OCH_2CH_3$ |
| 160 | $CF_2Cl$ | $CF_3$ | CN | $C(O)OCH_2CH_3$ |
| 161 | $CF_3$ | H | $C(O)NH_2$ | $C(O)OCH_2CH_3$ |
| 162 | $CF_3$ | Cl | $C(O)NH_2$ | $C(O)OCH_2CH_3$ |
| 163 | $CF_3$ | Br | $C(O)NH_2$ | $C(O)OCH_2CH_3$ |
| 164 | $CF_3$ | F | $C(O)NH_2$ | $C(O)OCH_2CH_3$ |
| 165 | $CF_3$ | $CF_3$ | $C(O)NH_2$ | $C(O)OCH_2CH_3$ |
| 166 | $CF_2Cl$ | H | $C(O)NH_2$ | $C(O)OCH_2CH_3$ |
| 167 | $CF_2Cl$ | Cl | $C(O)NH_2$ | $C(O)OCH_2CH_3$ |
| 168 | $CF_2Cl$ | Br | $C(O)NH_2$ | $C(O)OCH_2CH_3$ |
| 169 | $CF_2Cl$ | F | $C(O)NH_2$ | $C(O)OCH_2CH_3$ |
| 170 | $CF_2Cl$ | $CF_3$ | $C(O)NH_2$ | $C(O)OCH_2CH_3$ |
| 171 | $CF_3$ | H | $C(S)NH_2$ | $C(O)OCH_2CH_3$ |
| 172 | $CF_3$ | Cl | $C(S)NH_2$ | $C(O)OCH_2CH_3$ |
| 173 | $CF_3$ | Br | $C(S)NH_2$ | $C(O)OCH_2CH_3$ |
| 174 | $CF_3$ | F | $C(S)NH_2$ | $C(O)OCH_2CH_3$ |
| 175 | $CF_3$ | $CF_3$ | $C(S)NH_2$ | $C(O)OCH_2CH_3$ |
| 176 | $CF_2Cl$ | H | $C(S)NH_2$ | $C(O)OCH_2CH_3$ |
| 177 | $CF_2Cl$ | Cl | $C(S)NH_2$ | $C(O)OCH_2CH_3$ |
| 178 | $CF_2Cl$ | Br | $C(S)NH_2$ | $C(O)OCH_2CH_3$ |
| 179 | $CF_2Cl$ | F | $C(S)NH_2$ | $C(O)OCH_2CH_3$ |
| 180 | $CF_2Cl$ | $CF_3$ | $C(S)NH_2$ | $C(O)OCH_2CH_3$ |
| 181 | $CF_3$ | H | CN | $CH_2OC(O)CH_3$ |
| 182 | $CF_3$ | Cl | CN | $CH_2OC(O)CH_3$ |
| 183 | $CF_3$ | Br | CN | $CH_2OC(O)CH_3$ |
| 184 | $CF_3$ | F | CN | $CH_2OC(O)CH_3$ |
| 185 | $CF_3$ | $CF_3$ | CN | $CH_2OC(O)CH_3$ |
| 186 | $CF_2Cl$ | H | CN | $CH_2OC(O)CH_3$ |
| 187 | $CF_2Cl$ | Cl | CN | $CH_2OC(O)CH_3$ |
| 188 | $CF_2Cl$ | Br | CN | $CH_2OC(O)CH_3$ |
| 189 | $CF_2Cl$ | F | CN | $CH_2OC(O)CH_3$ |
| 190 | $CF_2Cl$ | $CF_3$ | CN | $CH_2OC(O)CH_3$ |
| 191 | $CF_3$ | H | $C(O)NH_2$ | $CH_2OC(O)CH_3$ |
| 192 | $CF_3$ | Cl | $C(O)NH_2$ | $CH_2OC(O)CH_3$ |
| 193 | $CF_3$ | Br | $C(O)NH_2$ | $CH_2OC(O)CH_3$ |
| 194 | $CF_3$ | F | $C(O)NH_2$ | $CH_2OC(O)CH_3$ |
| 195 | $CF_3$ | $CF_3$ | $C(O)NH_2$ | $CH_2OC(O)CH_3$ |
| 196 | $CF_2Cl$ | H | $C(O)NH_2$ | $CH_2OC(O)CH_3$ |
| 197 | $CF_2Cl$ | Cl | $C(O)NH_2$ | $CH_2OC(O)CH_3$ |
| 198 | $CF_2Cl$ | Br | $C(O)NH_2$ | $CH_2OC(O)CH_3$ |
| 199 | $CF_2Cl$ | F | $C(O)NH_2$ | $CH_2OC(O)CH_3$ |
| 200 | $CF_2Cl$ | $CF_3$ | $C(O)NH_2$ | $CH_2OC(O)CH_3$ |
| 201 | $CF_3$ | H | $C(S)NH_2$ | $CH_2OC(O)CH_3$ |
| 202 | $CF_3$ | Cl | $C(S)NH_2$ | $CH_2OC(O)CH_3$ |
| 203 | $CF_3$ | Br | $C(S)NH_2$ | $CH_2OC(O)CH_3$ |
| 204 | $CF_3$ | F | $C(S)NH_2$ | $CH_2OC(O)CH_3$ |
| 205 | $CF_3$ | $CF_3$ | $C(S)NH_2$ | $CH_2OC(O)CH_3$ |
| 206 | $CF_2Cl$ | H | $C(S)NH_2$ | $CH_2OC(O)CH_3$ |
| 207 | $CF_2Cl$ | Cl | $C(S)NH_2$ | $CH_2OC(O)CH_3$ |
| 208 | $CF_2Cl$ | Br | $C(S)NH_2$ | $CH_2OC(O)CH_3$ |
| 209 | $CF_2Cl$ | F | $C(S)NH_2$ | $CH_2OC(O)CH_3$ |
| 210 | $CF_2Cl$ | $CF_3$ | $C(S)NH_2$ | $CH_2OC(O)CH_3$ |
| 211 | $CF_3$ | H | CN | $CH_2OC(O)CH(CH_3)_2$ |
| 212 | $CF_3$ | Cl | CN | $CH_2OC(O)CH(CH_3)_2$ |
| 213 | $CF_3$ | Br | CN | $CH_2OC(O)CH(CH_3)_2$ |
| 214 | $CF_3$ | F | CN | $CH_2OC(O)CH(CH_3)_2$ |
| 215 | $CF_3$ | $CF_3$ | CN | $CH_2OC(O)CH(CH_3)_2$ |
| 216 | $CF_2Cl$ | H | CN | $CH_2OC(O)CH(CH_3)_2$ |
| 217 | $CF_2Cl$ | Cl | CN | $CH_2OC(O)CH(CH_3)_2$ |
| 218 | $CF_2Cl$ | Br | CN | $CH_2OC(O)CH(CH_3)_2$ |
| 219 | $CF_2Cl$ | F | CN | $CH_2OC(O)CH(CH_3)_2$ |
| 220 | $CF_2Cl$ | $CF_3$ | CN | $CH_2OC(O)CH(CH_3)_2$ |
| 221 | $CF_3$ | H | $C(O)NH_2$ | $CH_2OC(O)CH(CH_3)_2$ |
| 222 | $CF_3$ | Cl | $C(O)NH_2$ | $CH_2OC(O)CH(CH_3)_2$ |
| 223 | $CF_3$ | Br | $C(O)NH_2$ | $CH_2OC(O)CH(CH_3)_2$ |
| 224 | $CF_3$ | F | $C(O)NH_2$ | $CH_2OC(O)CH(CH_3)_2$ |
| 225 | $CF_3$ | $CF_3$ | $C(O)NH_2$ | $CH_2OC(O)CH(CH_3)_2$ |
| 226 | $CF_2Cl$ | H | $C(O)NH_2$ | $CH_2OC(O)CH(CH_3)_2$ |
| 227 | $CF_2Cl$ | Cl | $C(O)NH_2$ | $CH_2OC(O)CH(CH_3)_2$ |
| 228 | $CF_2Cl$ | Br | $C(O)NH_2$ | $CH_2OC(O)CH(CH_3)_2$ |

TABLE P1-continued

Substituent definitions of $R^2$, $R^3$, $X_3$ and $R^1$:

| | $R^3$ | $X_3$ | $R^2$ | $R^1$ |
|---|---|---|---|---|
| 229 | $CF_2Cl$ | F | $C(O)NH_2$ | $CH_2OC(O)CH(CH_3)_2$ |
| 230 | $CF_2Cl$ | $CF_3$ | $C(O)NH_2$ | $CH_2OC(O)CH(CH_3)_2$ |
| 231 | $CF_3$ | H | $C(S)NH_2$ | $CH_2OC(O)CH(CH_3)_2$ |
| 232 | $CF_3$ | Cl | $C(S)NH_2$ | $CH_2OC(O)CH(CH_3)_2$ |
| 233 | $CF_3$ | Br | $C(S)NH_2$ | $CH_2OC(O)CH(CH_3)_2$ |
| 234 | $CF_3$ | F | $C(S)NH_2$ | $CH_2OC(O)CH(CH_3)_2$ |
| 235 | $CF_3$ | $CF_3$ | $C(S)NH_2$ | $CH_2OC(O)CH(CH_3)_2$ |
| 236 | $CF_2Cl$ | H | $C(S)NH_2$ | $CH_2OC(O)CH(CH_3)_2$ |
| 237 | $CF_2Cl$ | Cl | $C(S)NH_2$ | $CH_2OC(O)CH(CH_3)_2$ |
| 238 | $CF_2Cl$ | Br | $C(S)NH_2$ | $CH_2OC(O)CH(CH_3)_2$ |
| 239 | $CF_2Cl$ | F | $C(S)NH_2$ | $CH_2OC(O)CH(CH_3)_2$ |
| 240 | $CF_2Cl$ | $CF_3$ | $C(S)NH_2$ | $CH_2OC(O)CH(CH_3)_2$ |
| 241 | $CF_3$ | H | CN | $CH_2OC(O)C(CH_3)_3$ |
| 242 | $CF_3$ | Cl | CN | $CH_2OC(O)C(CH_3)_3$ |
| 243 | $CF_3$ | Br | CN | $CH_2OC(O)C(CH_3)_3$ |
| 244 | $CF_3$ | F | CN | $CH_2OC(O)C(CH_3)_3$ |
| 245 | $CF_3$ | $CF_3$ | CN | $CH_2OC(O)C(CH_3)_3$ |
| 246 | $CF_2Cl$ | H | CN | $CH_2OC(O)C(CH_3)_3$ |
| 247 | $CF_2Cl$ | Cl | CN | $CH_2OC(O)C(CH_3)_3$ |
| 248 | $CF_2Cl$ | Br | CN | $CH_2OC(O)C(CH_3)_3$ |
| 249 | $CF_2Cl$ | F | CN | $CH_2OC(O)C(CH_3)_3$ |
| 250 | $CF_2Cl$ | $CF_3$ | CN | $CH_2OC(O)C(CH_3)_3$ |
| 251 | $CF_3$ | H | $C(O)NH_2$ | $CH_2OC(O)C(CH_3)_3$ |
| 252 | $CF_3$ | Cl | $C(O)NH_2$ | $CH_2OC(O)C(CH_3)_3$ |
| 253 | $CF_3$ | Br | $C(O)NH_2$ | $CH_2OC(O)C(CH_3)_3$ |
| 254 | $CF_3$ | F | $C(O)NH_2$ | $CH_2OC(O)C(CH_3)_3$ |
| 255 | $CF_3$ | $CF_3$ | $C(O)NH_2$ | $CH_2OC(O)C(CH_3)_3$ |
| 256 | $CF_2Cl$ | H | $C(O)NH_2$ | $CH_2OC(O)C(CH_3)_3$ |
| 257 | $CF_2Cl$ | Cl | $C(O)NH_2$ | $CH_2OC(O)C(CH_3)_3$ |
| 258 | $CF_2Cl$ | Br | $C(O)NH_2$ | $CH_2OC(O)C(CH_3)_3$ |
| 259 | $CF_2Cl$ | F | $C(O)NH_2$ | $CH_2OC(O)C(CH_3)_3$ |
| 260 | $CF_2Cl$ | $CF_3$ | $C(O)NH_2$ | $CH_2OC(O)C(CH_3)_3$ |
| 261 | $CF_3$ | H | $C(S)NH_2$ | $CH_2OC(O)C(CH_3)_3$ |
| 262 | $CF_3$ | Cl | $C(S)NH_2$ | $CH_2OC(O)C(CH_3)_3$ |
| 263 | $CF_3$ | Br | $C(S)NH_2$ | $CH_2OC(O)C(CH_3)_3$ |
| 264 | $CF_3$ | F | $C(S)NH_2$ | $CH_2OC(O)C(CH_3)_3$ |
| 265 | $CF_3$ | $CF_3$ | $C(S)NH_2$ | $CH_2OC(O)C(CH_3)_3$ |
| 266 | $CF_2Cl$ | H | $C(S)NH_2$ | $CH_2OC(O)C(CH_3)_3$ |
| 267 | $CF_2Cl$ | Cl | $C(S)NH_2$ | $CH_2OC(O)C(CH_3)_3$ |
| 268 | $CF_2Cl$ | Br | $C(S)NH_2$ | $CH_2OC(O)C(CH_3)_3$ |
| 269 | $CF_2Cl$ | F | $C(S)NH_2$ | $CH_2OC(O)C(CH_3)_3$ |
| 270 | $CF_2Cl$ | $CF_3$ | $C(S)NH_2$ | $CH_2OC(O)C(CH_3)_3$ |

Table B-1 provides 270 compounds B-1.001 to B-1.270 of formula (Id) wherein X2 is N, X1 is H and $R^1$, $R^2$, $R^3$ and $X_3$ are as defined in table P1.

Table B-2 provides 270 compounds B-2.001 to B-2.270 of formula (Id) wherein X2 is N, X1 is Cl and $R^1$, $R^2$, $R^3$ and $X_3$ are as defined in table P1.

Table B-3 provides 270 compounds B-3.001 to B-3.270 of formula (Id) wherein X2 is N, X1 is Br and $R^1$, $R^2$, $R^3$ and $X_3$ are as defined in table P1.

Table B-4 provides 270 compounds B-4.001 to B-4.270 of formula (Id) wherein X2 is N, X1 is F and $R^1$, $R^2$, $R^3$ and $X_3$ are as defined in table P1.

Table B-5 provides 270 compounds B-5.001 to B-5.270 of formula (Id) wherein X2 is N, X1 is $CF_3$ and $R^1$, $R^2$, $R^3$ and $X_3$ are as defined in table P1.

Table B-6 provides 270 compounds B-6.001 to B-6.270 of formula (Id) wherein X2 is C—H, X1 is H and $R^1$, $R^2$, $R^3$ and $X_3$ are as defined in table P1.

Table B-7 provides 270 compounds B-7.001 to B-7.270 of formula (Id) wherein X2 is C—H, X1 is Cl and $R^1$, $R^2$, $R^3$ and $X_3$ are as defined in table P1.

Table B-8 provides 270 compounds B-8.001 to B-8.270 of formula (Id) wherein X2 is C—H, X1 is Br and $R^1$, $R^2$, $R^3$ and $X_3$ are as defined in table P1.

Table B-9 provides 270 compounds B-9.001 to B-9.270 of formula (Id) wherein X2 is C—H, X1 is F and $R^1$, $R^2$, $R^3$ and $X_3$ are as defined in table P1.

Table B-10 provides 270 compounds B-10.001 to B-10.270 of formula (Id) wherein X2 is C—H, X1 is $CF_3$ and $R^1$, $R^2$, $R^3$ and $X_3$ are as defined in table P1.

Table B-11 provides 270 compounds B-11.001 to B-11.270 of formula (Id) wherein X2 is C—Cl, X1 is H and $R^1$, $R^2$, $R^3$ and $X_3$ are as defined in table P1.

Table B-12 provides 270 compounds B-12.001 to B-12.270 of formula (Id) wherein X2 is C—Cl, X1 is Cl and $R^1$, $R^2$, $R^3$ and $X_3$ are as defined in table P1.

Table B-13 provides 270 compounds B-13.001 to B-13.270 of formula (Id) wherein X2 is C—Cl, X1 is Br and $R^1$, $R^2$, $R^3$ and $X_3$ are as defined in table P1.

Table B-14 provides 270 compounds B-14.001 to B-14.270 of formula (Id) wherein X2 is C—Cl, X1 is F and $R^1$, $R^2$, $R^3$ and $X_3$ are as defined in table P1.

Table B-15 provides 270 compounds B-15.001 to B-15.270 of formula (Id) wherein X2 is C—Cl, X1 is $CF_3$ and $R^1$, $R^2$, $R^3$ and $X_3$ are as defined in table P1.

Table B-16 provides 270 compounds B-16.001 to B-16.270 of formula (Id) wherein X2 is C—Br, X1 is H and $R^1$, $R^2$, $R^3$ and $X_3$ are as defined in table P1.

Table B-17 provides 270 compounds B-17.001 to B-17.270 of formula (Id) wherein X2 is C—Br, X1 is Cl and $R^1$, $R^2$, $R^3$ and $X_3$ are as defined in table P1.

Table B-18 provides 270 compounds B-18.001 to B-18.270 of formula (Id) wherein X2 is C—Br, X1 is Br and $R^1$, $R^2$, $R^3$ and $X_3$ are as defined in table P1.

Table B-19 provides 270 compounds B-19.001 to B-19.270 of formula (Id) wherein X2 is C—Br, X1 is F and $R^1$, $R^2$, $R^3$ and $X_3$ are as defined in table P1.

Table B-20 provides 270 compounds B-20.001 to B-20.270 of formula (Id) wherein X2 is C—Br, X1 is $CF_3$ and $R^1$, $R^2$, $R^3$ and $X_3$ are as defined in table P1.

Table B-21 provides 270 compounds B-21.001 to B-21.270 of formula (Id) wherein X2 is C—F, X1 is H and $R^1$, $R^2$, $R^3$ and $X_3$ are as defined in table P1.

Table B-22 provides 270 compounds B-22.001 to B-22.270 of formula (Id) wherein X2 is C—F, X1 is Cl and $R^1$, $R^2$, $R^3$ and $X_3$ are as defined in table P1.

Table B-23 provides 270 compounds B-23.001 to B-23.270 of formula (Id) wherein X2 is C—F, X1 is Br and $R^1$, $R^2$, $R^3$ and $X_3$ are as defined in table P1.

Table B-24 provides 270 compounds B-24.001 to B-24.270 of formula (Id) wherein X2 is C—F, X1 is F and $R^1$, $R^2$, $R^3$ and $X_3$ are as defined in table P1.

Table B-25 provides 270 compounds B-25.001 to B-25.270 of formula (Id) wherein X2 is C—F, X1 is $CF_3$ and $R^1$, $R^2$, $R^3$ and $X_3$ are as defined in table P1.

Table B-26 provides 270 compounds B-26.001 to B-26.270 of formula (Id) wherein X2 is C—$CF_3$, X1 is H and $R^1$, $R^2$, $R^3$ and $X_3$ are as defined in table P1.

Table B-27 provides 270 compounds B-27.001 to B-27.270 of formula (Id) wherein X2 is C—$CF_3$, X1 is Cl and $R^1$, $R^2$, $R^3$ and $X_3$ are as defined in table P1.

Table B-28 provides 270 compounds B-28.001 to B-28.270 of formula (Id) wherein X2 is C—$CF_3$, X1 is Br and $R^1$, $R^2$, $R^3$ and $X_3$ are as defined in table P1.

Table B-29 provides 270 compounds B-29.001 to B-29.270 of formula (Id) wherein X2 is C—$CF_3$, X1 is F and $R^1$, $R^2$, $R^3$ and $X_3$ are as defined in table P1.

Table B-30 provides 270 compounds B-30.001 to B-30.270 of formula (Id) wherein X2 is C—$CF_3$, X1 is $CF_3$ and $R^1$, $R^2$, $R^3$ and $X_3$ are as defined in table P1.

The invention is further illustrated by making available the following individual compounds of formula (Ie) listed in Tables C-1 to C-270

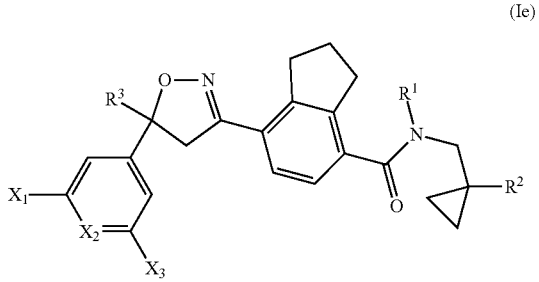

(Ie)

Table C-1 provides 270 compounds C-1.001 to C-1.270 of formula (Ie) wherein X2 is N, X1 is H and $R^1$, $R^2$, $R^3$ and $X_3$ are as defined in table P1.

Table C-2 provides 270 compounds C-2.001 to C-2.270 of formula (Ie) wherein X2 is N, X1 is Cl and $R^1$, $R^2$, $R^3$ and $X_3$ are as defined in table P1.

Table C-3 provides 270 compounds C-3.001 to C-3.270 of formula (Ie) wherein X2 is N, X1 is Br and $R^1$, $R^2$, $R^3$ and $X_3$ are as defined in table P1.

Table C-4 provides 270 compounds C-4.001 to C-4.270 of formula (Ie) wherein X2 is N, X1 is F and $R^1$, $R^2$, $R^3$ and $X_3$ are as defined in table P1.

Table C-5 provides 270 compounds C-5.001 to C-5.270 of formula (Ie) wherein X2 is N, X1 is $CF_3$ and $R^1$, $R^2$, $R^3$ and $X_3$ are as defined in table P1.

Table C-6 provides 270 compounds C-6.001 to C-6.270 of formula (Ie) wherein X2 is C—H, X1 is H and $R^1$, $R^2$, $R^3$ and $X_3$ are as defined in table P1.

Table C-7 provides 270 compounds C-7.001 to C-7.270 of formula (Ie) wherein X2 is C—H, X1 is Cl and $R^1$, $R^2$, $R^3$ and $X_3$ are as defined in table P1.

Table C-8 provides 270 compounds C-8.001 to C-8.270 of formula (Ie) wherein X2 is C—H, X1 is Br and $R^1$, $R^2$, $R^3$ and $X_3$ are as defined in table P1.

Table C-9 provides 270 compounds C-9.001 to C-9.270 of formula (Ie) wherein X2 is C—H, X1 is F and $R^1$, $R^2$, $R^3$ and $X_3$ are as defined in table P1.

Table C-10 provides 270 compounds C-10.001 to C-10.270 of formula (Ie) wherein X2 is C—H, X1 is $CF_3$ and $R^1$, $R^2$, $R^3$ and $X_3$ are as defined in table P1.

Table C-11 provides 270 compounds C-11.001 to C-11.270 of formula (Ie) wherein X2 is C—Cl, X1 is H and $R^1$, $R^2$, $R^3$ and $X_3$ are as defined in table P1.

Table C-12 provides 270 compounds C-12.001 to C-12.270 of formula (Ie) wherein X2 is C—Cl, X1 is Cl and $R^1$, $R^2$, $R^3$ and $X_3$ are as defined in table P1.

Table C-13 provides 270 compounds C-13.001 to C-13.270 of formula (Ie) wherein X2 is C—Cl, X1 is Br and $R^1$, $R^2$, $R^3$ and $X_3$ are as defined in table P1.

Table C-14 provides 270 compounds C-14.001 to C-14.270 of formula (Ie) wherein X2 is C—Cl, X1 is F and $R^1$, $R^2$, $R^3$ and $X_3$ are as defined in table P1.

Table C-15 provides 270 compounds C-15.001 to C-15.270 of formula (Ie) wherein X2 is C—Cl, X1 is $CF_3$ and $R^1$, $R^2$, $R^3$ and $X_3$ are as defined in table P1.

Table C-16 provides 270 compounds C-16.001 to C-16.270 of formula (Ie) wherein X2 is C—Br, X1 is H and $R^1$, $R^2$, $R^3$ and $X_3$ are as defined in table P1.

Table C-17 provides 270 compounds C-17.001 to C-17.270 of formula (Ie) wherein X2 is C—Br, X1 is Cl and $R^1$, $R^2$, $R^3$ and $X_3$ are as defined in table P1.

Table C-18 provides 270 compounds C-18.001 to C-18.270 of formula (Ie) wherein X2 is C—Br, X1 is Br and $R^1$, $R^2$, $R^3$ and $X_3$ are as defined in table P1.

Table C-19 provides 270 compounds C-19.001 to C-19.270 of formula (Ie) wherein X2 is C—Br, X1 is F and $R^1$, $R^2$, $R^3$ and $X_3$ are as defined in table P1.

Table C-20 provides 270 compounds C-20.001 to C-20.270 of formula (Ie) wherein X2 is C—Br, X1 is $CF_3$ and $R^1$, $R^2$, $R^3$ and $X_3$ are as defined in table P1.

Table C-21 provides 270 compounds C-21.001 to C-21.270 of formula (Ie) wherein X2 is C—F, X1 is H and $R^1$, $R^2$, $R^3$ and $X_3$ are as defined in table P1.

Table C-22 provides 270 compounds C-22.001 to C-22.270 of formula (Ie) wherein X2 is C—F, X1 is Cl and $R^1$, $R^2$, $R^3$ and $X_3$ are as defined in table P1.

Table C-23 provides 270 compounds C-23.001 to C-23.270 of formula (Ie) wherein X2 is C—F, X1 is Br and $R^1$, $R^2$, $R^3$ and $X_3$ are as defined in table P1.

Table C-24 provides 270 compounds C-24.001 to C-24.270 of formula (Ie) wherein X2 is C—F, X1 is F and $R^1$, $R^2$, $R^3$ and $X_3$ are as defined in table P1.

Table C-25 provides 270 compounds C-25.001 to C-25.270 of formula (Ie) wherein X2 is C—F, X1 is $CF_3$ and $R^1$, $R^2$, $R^3$ and $X_3$ are as defined in table P1.

Table C-26 provides 270 compounds C-26.001 to C-26.270 of formula (Ie) wherein X2 is C—$CF_3$, X1 is H and $R^1$, $R^2$, $R^3$ and $X_3$ are as defined in table P1.

Table C-27 provides 270 compounds C-27.001 to C-27.270 of formula (Ie) wherein X2 is C—$CF_3$, X1 is Cl and $R^1$, $R^2$, $R^3$ and $X_3$ are as defined in table P1.

Table C-28 provides 270 compounds C-28.001 to C-28.270 of formula (Ie) wherein X2 is C—$CF_3$, X1 is Br and $R^1$, $R^2$, $R^3$ and $X_3$ are as defined in table P1.

Table C-29 provides 270 compounds C-29.001 to C-29.270 of formula (Ie) wherein X2 is C—$CF_3$, X1 is F and $R^1$, $R^2$, $R^3$ and $X_3$ are as defined in table P1.

Table C-30 provides 270 compounds C-30.001 to C-30.270 of formula (Ie) wherein X2 is C—$CF_3$, X1 is $CF_3$ and $R^1$, $R^2$, $R^3$ and $X_3$ are as defined in table P1.

The compounds of formula (I) according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

Agriotes spp., Amphimallon majale, Anomala orientalis, Anthonomus spp., Aphodius spp, Astylus atromaculatus, Ataenius spp, Atomaria linearis, Chaetocnema tibialis, Cerotoma spp, Conoderus spp, Cosmopolites spp., Cotinis nitida, Curculio spp., Cyclocephala spp, Dermestes spp., Diabrotica spp., Diloboderus abderus, Epilachna spp., Eremnus spp., Heteronychus arator, Hypothenemus hampei, Lagria vilosa, Leptinotarsa decemLineata, Lissorhoptrus spp., Liogenys spp, Maecolaspis spp, Maladera castanea, Megascelis spp, Melighetes aeneus, Melolontha spp., Myochrous armatus, Orycaephilus spp., Otiorhynchus spp., Phyllophaga spp, Phlyctinus spp., Popillia spp., Psylliodes spp., Rhyssomatus aubtilis, Rhizopertha spp., Scarabeidae, Sitophilus spp., Sitotroga spp., Somaticus spp, Sphenophorus spp, Sternechus subsignatus, Tenebrio spp., Tribolium spp. and Trogoderma spp.;

from the order Diptera, for example,

Aedes spp., Anopheles spp, Antherigona soccata, Bactrocea oleae, Bibio hortulanus, Bradysia spp, Calliphora erythrocephala, Ceratitis spp., Chrysomyia spp., Culex spp., Cuterebra spp., Dacus spp., Delia spp, Drosophila melanogaster, Fannia spp., Gastrophilus spp., Geomyza tripunctata, Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis spp, Rivelia quadrifasciata, Scatella spp, Sciara spp., Stomoxys spp., Tabanus spp., Tannia spp. and Tipula spp.;

from the order Hemiptera, for example,

Acanthocoris scabrator, Acrosternum spp, Adelphocoris lineolatus, Amblypelta nitida, Bathycoelia thalassina, Blissus spp, Cimex spp., Clavigralla tomentosicollis, Creontiades spp, Distantiella theobroma, Dichelops furcatus, Dysdercus spp., Edessa spp, Euchistus spp., Eurydema pulchrum, Eurygaster spp., Halyomorpha halys, Horcias nobilellus, Leptocorisa spp., Lygus spp, Margarodes spp, Murgantia histrionic, Neomegalotomus spp, Nesidiocoris tenuis, Nezara spp., Nysius simulans, Oebalus insularis, Piesma spp., Piezodorus spp, Rhodnius spp., Sahlbergella singularis, Scaptocoris castanea, Scotinophara spp., Thyanta spp, Triatoma spp., Vatiga illudens; Acyrthosium pisum, Adalges spp, Agalliana ensigera, Agonoscena targionii, Aleurodicus spp, Aleurocanthus spp, Aleurolobus barodensis, Aleurothrixus floccosus, Aleyrodes brassicae, Amarasca biguttula, Amritodes atkinsoni, Aonidiella spp., Aphididae, Aphis spp., Aspidiotus spp., Aulacorthum solani, Bactericera cockerelli, Bemisia spp, Brachycaudus spp, Brevicoryne brassicae, Cacopsylla spp, Cavariella aegopodii Scop., Ceroplaster spp., Chrysomphalus aonidium, Chrysomphalus dictyospermi, Cicadella spp, Cofana spectra, Cryptomyzus spp, Cicadulina spp, Coccus hesperidum, Dalbulus maidis, Dialeurodes spp, Diaphorina citri, Diuraphis noxia, Dysaphis spp, Empoasca spp., Eriosoma larigerum, Erythroneura spp., Gascardia spp., Glycaspis brimblecombei, Hyadaphis pseudobrassicae, Hyalopterus spp., Hyperomyzus pallidus, Idioscopus clypealis, Jacobiasca lybica, Laodelphax spp., Lecanium corni, Lepidosaphes spp., Lopaphis erysimi, Lyogenys maidis, Macrosiphum spp., Mahanarva spp, Metcalfa pruinosa, Metopolophium dirhodum, Myndus crudus, Myzus spp., Neotoxoptera sp, Nephotettix spp., Nilaparvata spp., Nippolachnus piri Mats, Odonaspis ruthae, Oregma lanigera Zehnter, Parabemisia myricae, Paratrioza cockerelli, Parlatoria spp., Pemphigus spp., Peregrinus maidis, Perkinsiella spp., Phorodon humuli, Phylloxera spp., Planococcus spp., Pseudaulacaspis spp., Pseudococcus spp., Pseudatomoscelis seriatus, Psylla spp., Pulvinaria aethiopica, Quadraspidiotus spp., Quesada gigas, Recilia dorsalis, Rhopalosiphum spp., Saissetia spp., Scaphoideus spp., Schizaphis spp., Sitobion spp., Sogatella furcifera, Spissistilus festinus, Tarophagus Proserpina, Toxoptera spp, Trialeurodes spp, Tridiscus sporoboli, Trionymus spp, Trioza erytreae, Unaspis citri, Zygina flammigera, Zyginidia scutellaris;

from the order Hymenoptera, for example,

Acromyrmex, Arge spp., Atta spp., Cephus spp., Diprion spp., Diprionidae, Gilpinia polytoma, Hoplo-campa spp., Lasius spp., Monomorium pharaonis, Neodiprion spp., Pogonomyrmex spp, Slenopsis invicta, Solenopsis spp. and Vespa spp.;

from the order Isoptera, for example,

Coptotermes spp, Corniternes cumulans, Incisitermes spp, Macrotermes spp, Mastotermes spp, Microtermes spp, Reticulitermes spp.; Solenopsis geminate from the order Lepidoptera, for example, Acleris spp., Adoxophyes spp., Aegeria spp., Agrotis spp., Alabama argillaceae, Amylois spp., Anticarsia gemmatalis, Archips spp., Argyresthia spp., Argyrotaenia spp., Autographa spp., Bucculatrix thurberiella, Busseola fusca, Cadra cautella, Carposina nipponensis, Chilo spp., Choristoneura spp., Chrysoteuchia topiaria, Clysia ambiguella, Cnaphalocrocis spp., Cnephasia spp., Cochylis spp., Coleophora spp., Colias lesbia, Cosmophila flava, Crambus spp, Crocidolomia binotalis, Cryptophlebia leucotreta, Cydalima perspectalis, Cydia spp., Diaphania perspectalis, Diatraea spp., Diparopsis castanea, Earias spp., Eldana saccharina, Ephestia spp., Epinotia spp, Estigmene acrea, Etiella zinckinella, Eucosma spp., Eupoecilia ambiguella, Euproctis spp., Euxoa spp., Feltia jaculiferia, Grapholita spp., Hedya nubiferana, Heliothis spp., Hellula undalis, Herpetogramma spp, Hyphantria cunea, Keiferia lycopersicella, Lasmopalpus lignosellus, Leucoptera scitella, Lithocollethis spp., Lobesia botrana, Loxostege bifidalis, Lymantria spp., Lyonetia spp., Malacosoma spp., Mamestra brassicae, Manduca sexta, Mythimna spp, Noctua spp, Operophtera spp., Orniodes indica, Ostrinia nubilalis, Pammene spp., Pandemis spp., Panolis flammea, Papaipema nebris, Pectinophora gossypi-ela, Perileucoptera coffeella, Pseudaletia unipuncta, Phthorimaea operculella, Pieris rapae, Pieris spp., Plutella xylostella, Prays spp., Pseudoplusia spp, Rachiplusia nu, Richia albicosta, Scirpophaga spp., Sesamia spp., Sparganothis spp., Spodoptera spp., Sylepta derogate, Synanthedon spp., Thaumetopoea spp., Tortrix spp., Trichoplusia ni, Tuta absoluta, and Yponomeuta spp.;

from the order Mallophaga, for example,

Damalinea spp. and Trichodectes spp.;

from the order Orthoptera, for example,

Blatta spp., Blattella spp., Gryllotalpa spp., Leucophaea maderae, Locusta spp., Neocurtilla hexadactyla, Periplaneta spp., Scapteriscus spp, and Schistocerca spp.;

from the order Psocoptera, for example,

Liposcelis spp.;

from the order Siphonaptera, for example,

Ceratophyllus spp., Ctenocephalides spp. and Xenopsylla cheopis;

from the order Thysanoptera, for example,

Calliothrips phaseoli, Frankliniella spp., Heliothrips spp, Hercinothrips spp., Parthenothrips spp, Scirtothrips aurantii, Sericothrips variabilis, Taeniothrips spp., Thrips spp;

from the order Thysanura, for example,

Lepisma saccharina.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum*, *A. cepa*, *A. oschaninii*, *A. Porrum*, *A. ascalonicum*, *A. fistulosum*), *Anthriscus cerefolium*, *Apium graveolus*, *Asparagus officinalis*, *Beta vulgarus*, *Brassica* spp. (*B. Oleracea*, *B. Pekinensis*, *B. rapa*), *Capsicum annuum*, *Cicer arietinum*, *Cichorium endivia*, *Cichorum* spp. (*C. intybus*, *C. endivia*), *Citrillus lanatus*, *Cucumis* spp. (*C. sativus*, *C. melo*), *Cucurbita* spp. (*C. pepo*, *C. maxima*), *Cyanara* spp. (*C. scolymus*, *C. cardunculus*), *Daucus carota*, *Foeniculum vulgare*, *Hypericum* spp., *Lactuca sativa*, *Lycopersicon* spp. (*L. esculentum*, *L. lycopersicum*), *Mentha* spp., *Ocimum basilicum*, *Petroselinum crispum*, *Phaseolus* spp. (*P. vulgaris*, *P. coccineus*), *Pisum sativum*, *Raphanus sativus*, *Rheum rhaponticum*, *Rosemarinus* spp., *Salvia* spp., *Scorzonera hispanica*, *Solanum melongena*, *Spinacea oleracea*, *Valerianella* spp. (*V. locusta*, *V. eriocarpa*) and *Vicia faba*.

Preferred ornamental species include African violet, *Begonia*, *Dahlia*, *Gerbera*, *Hydrangea*, *Verbena*, *Rosa*, *Kalanchoe*, *Poinsettia*, *Aster*, *Centaurea*, *Coreopsis*, *Delphinium*, *Monarda*, *Phlox*, *Rudbeckia*, *Sedum*, *Petunia*, *Viola*, *Impatiens*, *Geranium*, *Chrysanthemum*, *Ranunculus*, *Fuchsia*, *Salvia*, *Hortensia*, rosemary, sage, St. Johnswort, mint, sweet pepper, tomato and cucumber.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater*, *A. circumscriptus*, *A. hortensis*, *A. rufus*); Bradybaenidae (*Bradybaena fruticum*); Cepaea (*C. hortensis*, *C. Nemoralis*); ochlodina; Deroceras (*D. agrestis*, *D. empiricorum*, *D. laeve*, *D. reticulatum*); Discus (*D. rotundatus*); Euomphalia; Galba (*G. trunculata*); Helicelia (*H. itala*, *H. obvia*); Helicidae

*Helicigona arbustorum*); Helicodiscus; Helix (*H. aperta*); Limax (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); Vallonia and Zanitoides.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula (I).

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, *Sassafras*, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, *Viburnum*, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |

TABLE B-continued

Examples of native woodborers of economic importance.

| Family | Species | Host or Crop Infested |
| --- | --- | --- |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, *Viburnum*, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm Pseudaletia *unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes*

*indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula (I) with active ingredients are preferred (the abbreviation "TX" means "one compound selected from the group consisting of the compounds described in Table 1 to 162, B-1 to B-270, C-1 to C-270, A, B and F of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fen-pyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, ometthoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, Neodiprion sertifer NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2, 13-dien-1-yl acetate (IUPAC name) (588)+TX, octadeca-3, 13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3, 4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, I (696)+TX, jasmolin II (696)+TX, jodfenphos (1248)+TX, juvenile hormone I (alternative name) [CCN]+TX, juvenile hormone II (alternative name) [CCN]+TX, juvenile hormone Ill (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine

[108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimetho-morph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a, 12,12a, 12b-decahydro-6,12-dihyd roxy-4,6a, 12b-trimethyl-11-oxo-9-(3-pyridinyl)-2H, 11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methyl-propyl)-4-[2,2,2-trifluoro-1-methoxy-1-(trifluoromethyl) ethyl]phenyl]-1H-pyrazole-4-carboxamide [926914-55-8]+TX; lancotrione [1486617-21-3]+TX, florpyrauxifen [943832-81-3]]+TX, ipfentrifluconazole[1417782-08-1]+TX, mefentrifluconazole [1417782-03-6]+TX, quinofumelin [861647-84-9]+TX, chloroprallethrin [399572-87-3]+TX, cyhalodiamide [1262605-53-7]]+TX, fluazaindolizine [1254304-22-7]+TX, fluxametamide [928783-29-3]+TX, epsilon-metofluthrin [240494-71-7]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1]+TX, kappa-tefluthrin [391634-71-2]+TX, fenpicoxamid [517875-34-2]+TX; fluindapyr [1383809-87-7]+TX; alpha-bromadiolone [28772-56-7]+TX; flupyrimin [1689566-03-7]+TX; benzpyrimoxan [1449021-97-9]+TX; acynonapyr [1332838-17-1]+TX; inpyrfluxam [1352994-67-2]+TX, isoflucypram [1255734-28-1]+TX; rescalure [64309-03-1]+TX; aminopyrifen [1531626-08-0]+TX; tyclopyrazoflor [1477919-27-9]+TX; and spiropidion [1229023-00-0]+TX; and microbials including: *Acinetobacter iwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* CrylAb+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (Xen- Tari®)+TX, DiPel®)+TX, bacteria spp. (GROWMEND®+TX, GROWSWEET®+TX, Shootup®)+TX, bacteriophage of Clavipactermichiganensis (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida* tenius+TX, Cedecea dravisae+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella* granulovirus (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone–formononetin (Myconate®)+TX, *Kloeckera* apiculata+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (*Muscudor*®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (*Econem*®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas* corrugate+TX, *Pseudomonas fluorescens* strain A506 (BlightBan A506®)+TX, *Pseudomonas putida*+TX, *Pseudomonas* reactans+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia* minor+TX, *Sclerotinia* minor (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, Sporobolomyces *roseus*+TX, *Stenotrophomonas maltophilia*+TX, *Streptomyces* ahygroscopicus+TX, *Streptomyces albaduncus*+TX, *Streptomyces* exfoliates+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX, E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus* lounsburyi+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX,

*Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from 1 to 162, B-1 to B-270, C-1 to C-270, A, B and F with active ingredients described above comprises a compound selected from Table 1 to 162, B-1 to B-270, C-1 to C-270, A, B and F and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from Table 1 to 162, B-1 to B-270, C-1 to C-270, A, B and F and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Table 1 to 162, B-1 to B-270, C-1 to C-270, A, B and F and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds of formula (I) for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula (I). The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| active ingredient | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredient | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm, 0.4 ppm, 0.2 ppm, 0.1 ppm or even at lower concentrations.

PREPARATORY EXAMPLES

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.

The following LC-MS methods were used to characterize the compounds:
Method J

Waters Aquity UPLC-MS using a Sample Organizer with Sample Manager FTN, H-class QSM, Column Manager, 2 × Column Manager Aux, photodiode array, ELSD and SOD 2 equipped with a Waters HSS T3 C18 column (column length 30 mm, internal diameter of column 2.1 mm, particle size 1.8 micron). The analysis was conducted using a two minute run time, according to the following gradient table:

| Time (mins) | Solvent A (%) | Solvent B (%) | Flow (ml/mn) |
|---|---|---|---|
| 0 | 95 | 5 | 0.7 |
| 1.75 | 0 | 100 | 0.7 |
| 1.76 | 0 | 100 | 0.7 |
| 2 | 0 | 5 | 0.7 |
| 2.01 | 95 | 5 | 0.7 |
| 2.11 | 95 | 5 | 0.7 |

Solvent A: H$_2$O with 0.05% trifluoroacetic acid (TFA)
Solvent B: CH$_3$CN with 0.05% trifluoroacetic acid (TFA)

Example 1: N-[(1-cyanocyclopropyl)methyl]-4-[(5S)-5-(3,5-dichloro-4-fluoro-phenyl)-5-(trifluoromethyl)-4H-isoxazol-3-yl]-2-methyl-benzamide (Example A01 in Table A)

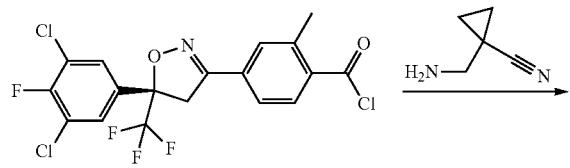

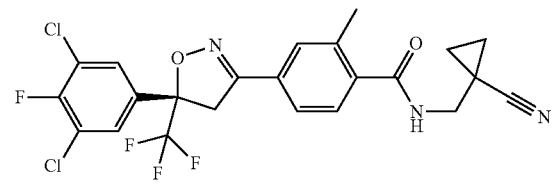

A suspension of the hydrochloride salt of 1-(aminomethyl)cyclopropanecarbonitrile (0.53 g) in dichloromethane (36 ml) was treated with triethylamine (0.74 g) and stirred at 20° C. To this solution, a solution 4-[(5S)-5-(3,5-dichloro-4-fluoro-phenyl)-5-(trifluoromethyl)-4H-isoxazol-3-yl]-2-methyl-benzoyl chloride (11 mL, 0.33M in toluene) (the preparation of 4-[5-(3,5-dichloro-4-fluoro-phenyl)-5-(trifluoromethyl)-4H-isoxazol-3-yl]-2-methyl-benzoic acid is described in WO2013/026695) was slowly added. The mixture was stirred for 24 hours then it was diluted with ethyl acetate and a solution of HCl (0.5 M). The phases were separated and the aqueous layer was extracted with ethyl acetate. The organic phases were combined, dried over sodium sulfate, filtered and evaporated to yield a crude product which was further purified by chromatography over silica gel with ethyl acetate-cyclohexane mixture as an eluent (gradient from 0:1 to 1:0), to give the title compound (1.79 g) as a slightly white foam. $^1$H-NMR (CDCl$_3$, 400 MHz, δ in ppm): 1.12-1.24 (m, 2H) 1.31-1.40 (m, 2H) 2.50 (s, 3H) 3.56 (d, 2H) 3.71 (d, 1H) 4.10 (d, 1H) 6.28 (t, 1H) 7.42-7.51 (m, 1H) 7.47-7.57 (m, 2H) 7.60 (d, 2H).

Example 2: N-[(1-carbamothioylcyclopropyl)methyl]-4-[(5S)-5-(3,5-dichloro-4-fluoro-phenyl)-5-(trifluoromethyl)-4H-isoxazol-3-yl]-2-methyl-benzamide (Example B01 in Table A)

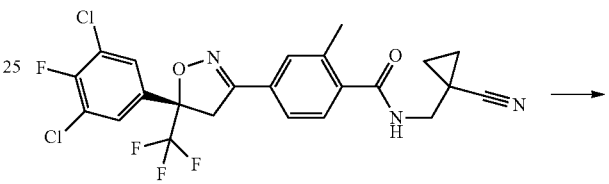

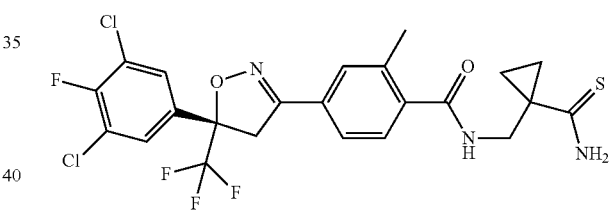

To a solution of N-[(1-cyanocyclopropyl)methyl]-4-[(5S)-5-(3,5-dichloro-4-fluoro-phenyl)-5-(trifluoromethyl)-4H-isoxazol-3-yl]-2-methyl-benzamide (0.20 g) dissolved in methanol (2.3 mL), was added a solution of ammonium sulfide 21% aq. (1.0 mL) and the solution was refluxed for 24 hours. Then some additional ammonium sulfide 21% aq. (0.50 g, 0.51 mL, 1.6 mmol) was added and the solution was refluxed for 5 hours. The solution was allowed to cool to room temperature and was diluted with ethyl acetate and water. The phases were separated and the aqueous layer was extracted with ethyl acetate. The organic phases were combined, dried over magnesium sulfate, filtered and evaporated to yield a crude product which was further purified by chromatography over silica gel with ethyl acetate-cyclohexane mixture as an eluent (gradient from 0:1 to 1:0), to give a mixture containing the title compound. This could be further purified on a preparative UPLC and through a second chromatography over silica gel to give the title compound (86 mg) as a slightly white solid. $^1$H-NMR (CDCl$_3$, 400 MHz, δ in ppm):

1.05-1.19 (m, 2H) 1.66-1.78 (m, 2H) 2.46 (s, 3H) 3.70 (d, 1H) 3.78 (d, 1H) 4.01-4.16 (m, 1H) 6.51 (t, 1H) 7.43 (d, 1H) 7.50-7.66 (m, 4H) 8.53 (br. s., 1H).

Example 3: N-[(1-carbamoylcyclopropyl)methyl]-4-[(5S)-5-(3,5-dichloro-4-fluoro-phenyl)-5-(trifluoromethyl)-4H-isoxazol-3-yl]-2-methyl-benzamide (Example C01 in Table A)

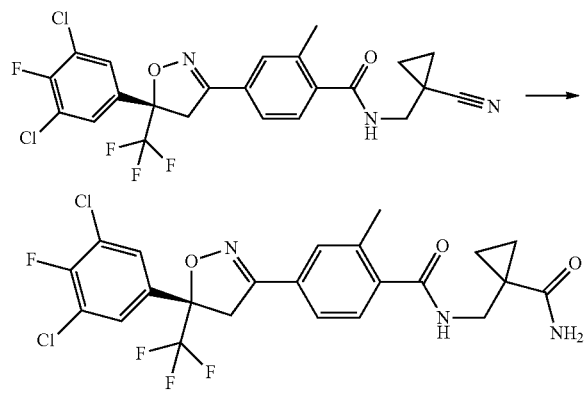

To a solution of N-[(1-cyanocyclopropyl)methyl]-4-[(5S)-5-(3,5-dichloro-4-fluoro-phenyl)-5-(trifluoromethyl)-4H-isoxazol-3-yl]-2-methyl-benzamide (1 g) dissolved in dimethyl sulfoxide (10 mL) at ambient temperature, was added potassium carbonate (0.19 g). The reaction mixture was then cooled to 0-5° C., and a solution of hydrogen peroxide 30% (1.4 mL) was added dropwise. The reaction mixture was then stirred at room temperature for 18 hours. The solution was diluted with ethyl acetate and an aqueous solution of hydrogen chloride (0.5 M). The phases were separated and the aqueous layer was extracted with ethyl acetate. The organic phases were combined, dried over magnesium sulfate and filtered. A peroxide test revealed the presence of residual peroxide in the organic phase, therefore they were treated with a solution of sodium bisulfite (~40% aq). The mixture was extracted again between ethyl acetate and water. The organic phases were combined, dried over magnesium sulfate, filtered and evaporated to yield a crude product which was further purified by chromatography over silica gel with ethyl acetate-cyclohexane mixture as an eluent (gradient from 0:1 to 1:0), to give the title compound (888 mg) as a slightly white foam. ¹H-NMR (CDCl₃, 400 MHz, δ in ppm): 0.84-0.94 (m, 2H) 1.27-1.35 (m, 2H) 2.47 (s, 3H) 3.60-3.76 (m, 3H) 4.03-4.13 (m, 1H) 6.44 (t, 1H) 7.36-7.46 (m, 1H) 7.48-7.55 (m, 2H) 7.59 (d, 2H)

Example 4: ethyl N-[(1-cyanocyclopropyl)methyl]-N-[4-[(5S)-5-(3,5-dichloro-4-fluoro-phenyl)-5-(trifluoromethyl)-4H-isoxazol-3-yl]-2-methyl-benzoyl] carbamate (Example F01 in Table F)

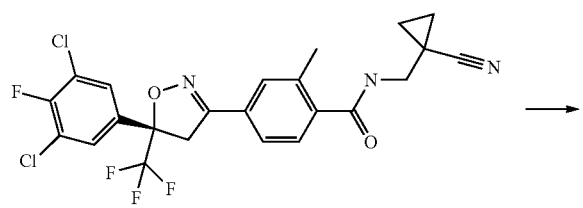

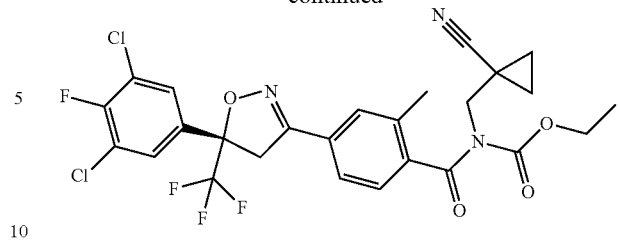

To a solution of N-[(1-cyanocyclopropyl)methyl]-4-[(5S)-5-(3,5-dichloro-4-fluoro-phenyl)-5-(trifluoromethyl)-4H-isoxazol-3-yl]-2-methyl-benzamide (0.50 g) dissolved in N,N-Dimethylformamide (9.7 mL) under argon was added by portions sodium hydride (60% suspension in paraffin oil, 0.043 g) and the reaction was stirred at room temperature for one hour. Then ethyl chloroformate (0.12 mL) was added and the reaction was stirred at room temperature for 23 h. The solution was diluted with ethyl acetate and water. The phases were separated and the organic phase was extracted further with a saturated solution of ammonium chloride. The organic phases were combined, dried over magnesium sulfate, filtered and evaporated to yield a crude product which was further purified by chromatography over silica gel with ethyl acetate-cyclohexane mixture as an eluent (gradient from 0:1 to 1:0), to give the title compound (249 mg) as a slightly white foam. ¹H-NMR (CDCl₃, 400 MHz, δ in ppm): 7.60 (d, 2H) 7.55 (s, 1H) 7.50-7.53 (m, 1H) 7.30 (d, 1H) 4.12 (q, 2H) 4.03-4.09 (m, 3H) 3.69 (d, 1H) 2.40 (s, 3H) 1.32-1.39 (m, 2H) 1.21-1.31 (m, 2H) 1.10 (t, 3H).

The other compounds were prepared in a similar manner.

TABLE A

Compounds of formula AA (AA)

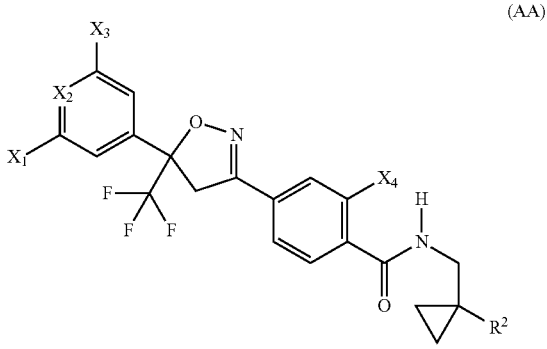

| Compound number | $X_1$ | $X_2$ | $X_3$ | $X_4$ | $R^2$ | stereochemistry at Isoxazoline ring |
|---|---|---|---|---|---|---|
| A01 | Cl | C—F | Cl | CH₃ | CN | enriched in S isomer |
| A02 | Cl | C—H | Cl | CH₃ | CN | enriched in S isomer |
| A03 | Cl | C—Cl | Cl | CH₃ | CN | enriched in S isomer |
| A04 | Cl | C—H | CF₃ | CH₃ | CN | enriched in S isomer |
| A05 | Cl | C—OMe | Cl | CH₃ | CN | enriched in S isomer |
| A06 | Cl | C—F | Cl | CH₃ | CN | racemic mixture |

TABLE A-continued

Compounds of formula AA

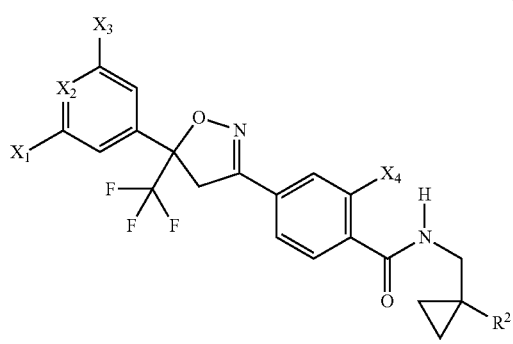

(AA)

| Compound number | $X_1$ | $X_2$ | $X_3$ | $X_4$ | $R^2$ | stereochemistry at Isoxazoline ring |
|---|---|---|---|---|---|---|
| A07 | $CF_3$ | C—Cl | $CF_3$ | $CH_3$ | CN | racemic mixture |
| A08 | F | C—Cl | H | $CH_3$ | CN | racemic mixture |
| A09 | Cl | C—Br | Cl | $CH_3$ | CN | racemic mixture |
| A10 | H | C—Br | H | $CH_3$ | CN | racemic mixture |
| A11 | H | C—$OCF_3$ | H | $CH_3$ | CN | racemic mixture |
| A12 | Cl | C—H | Cl | cPr | CN | racemic mixture |
| A13 | Cl | C—H | $CH_3$ | $CH_3$ | CN | racemic mixture |
| A14 | Cl | C—Cl | H | $CH_3$ | CN | racemic mixture |
| A15 | Cl | C—H | Cl | Cl | CN | racemic mixture |
| A16 | $CF_3$ | C—H | $CF_3$ | $CH_3$ | CN | racemic mixture |
| A17 | Cl | C—H | Cl | Br | CN | racemic mixture |
| A18 | CF3 | C—H | Br | $CH_3$ | CN | enriched in S isomer |
| A19 | CF3 | C—H | Cl | Cl | CN | enriched in S isomer |
| A20 | CF3 | C—H | H | $CH_3$ | CN | enriched in S isomer |
| A21 | Cl | C—Cl | Cl | Cl | CN | enriched in S isomer |
| A22 | Cl | C—F | Cl | Cl | CN | enriched in S isomer |
| A23 | Cl | C—Cl | Cl | Br | CN | enriched in S isomer |
| A24 | Cl | C—F | Cl | Br | CN | enriched in S isomer |
| B01 | Cl | C—F | Cl | $CH_3$ | $C(S)NH_2$ | enriched in S isomer |
| B02 | Cl | C—H | Cl | $CH_3$ | $C(S)NH_2$ | enriched in S isomer |
| C01 | Cl | C—F | Cl | $CH_3$ | $C(O)NH_2$ | enriched in S isomer |
| C02 | Cl | C—H | Cl | $CH_3$ | $C(O)NH_2$ | enriched in S isomer |

TABLE B

| Compound number | IUPAC name | Stereochemistry at Isoxazoline ring |
|---|---|---|
| D01 | N-[(1-cyanocyclopropyl)methyl]-5-[5-(3,5-dichlorophenyl)-5-(trifluoromethyl)-4H-isoxazol-3-yl]pyridine-2-carboxamide | racemic mixture |
| D02 | N-[(1-cyanocyclopropyl)methyl]-6-[5-(3,5-dichlorophenyl)-5-(trifluoromethyl)-4H-isoxazol-3-yl]-4-methyl-pyridine-3-carboxamide | racemic mixture |
| E01 | N-[1-(1-cyanocyclopropyl)ethyl]-4-[(5S)-5-(3,5-dichloro-4-fluoro-phenyl)-5-(trifluoromethyl)-4H-isoxazol-3-yl]-2-methyl-benzamide | enriched in S isomer |

TABLE F

Compounds of formula FF (FF)

| Compound number | X₁ | X₂ | X₃ | R¹ | stereochemistry at isoxazoline ring |
|---|---|---|---|---|---|
| F01 | Cl | C—F | Cl | C(O)OCH₂CH₃ | enriched in S isomer |
| F02 | Cl | C—F | Cl | C(O)(CH₃)₃ | enriched in S isomer |
| F03 | Cl | C—F | Cl | C(O)cPr | enriched in S isomer |
| F04 | Cl | C—F | Cl | C(O)OCH₃ | enriched in S isomer |
| F05 | Cl | C—F | Cl | SC(O)OCH₃ | enriched in S isomer |
| F06 | Cl | C—F | Cl | CH₂OC(O)CH(CH₃)₂ | enriched in S isomer |
| F07 | Cl | C—F | Cl | CH₂OC(O)CH₃ | enriched in S isomer |
| F08 | Cl | C—F | Cl | CH₂OCH₂CH₃ | enriched in S isomer |
| F09 | Cl | C—F | Cl | CH₂OCH₃ | enriched in S isomer |
| F10 | Cl | C—F | Cl | CH₂OC(O)(CH₃)₃ | enriched in S isomer |
| F11 | Cl | C—F | Cl | C(O)OCH₂Cl | enriched in S isomer |
| F12 | Cl | C—F | Cl | CH₂N(CH₃)C(O)OCH₃ | enriched in S isomer |

TABLE A1

(analytic data of the compounds of Table A):

| Compound number | LC-MS Method | RT (min) | [M + H]⁺ | ¹H NMR (400 MHz, CHLOROFORM-d) δ ppm |
|---|---|---|---|---|
| A01 | | | | 1.12-1.24 (m, 2 H) 1.31-1.40 (m, 2 H) 2.50 (s, 3 H) 3.56 (d, 2 H) 3.71 (d, 1 H) 4.10 (d, 1 H) 6.28 (t, 1 H) 7.42-7.51 (m, 1 H) 7.47-7.57 (m, 2 H) 7.60 (d, 2 H) |
| A02 | | | | 1.13-1.24 (m, 2 H) 1.31-1.40 (m, 2 H) 2.50 (s, 3 H) 3.56 (d, 2 H) 3.72 (d, 1 H) 4.03-4.15 (m, 1 H) 6.28 (t, 1 H) 7.40-7.51 (m, 2 H) 7.51-7.60 (m, 4 H) |
| A03 | | | | 1.13-1.23 (m, 2 H) 1.31-1.40 (m, 2 H) 2.51 (s, 3 H) 3.56 (d, 2 H) 3.71 (d, 1 H) 4.05-4.12 (m, 1 H) 6.24 (br. s., 1 H) 7.43-7.51 (m, 1 H) 7.50-7.58 (m, 2 H) 7.66 (s, 2 H) |
| A04 | | | | 1.15-1.24 (m, 2 H) 1.31-1.41 (m, 2 H) 2.51 (s, 3 H) 3.56 (d, 2 H) 3.74 (d, 1 H) 4.11-4.22 (m, 1 H) 6.26 (s, 1 H) 7.43-7.52 (m, 1 H) 7.52-7.60 (m, 2 H) 7.70 (s, 1 H) 7.77 (s, 1 H) 7.84 (s, 1 H) |
| A05 | | | | 1.09-1.22 (m, 2 H) 1.30-1.39 (m, 2 H) 2.50 (s, 3 H) 3.51-3.61 (m, 2 H) 3.65-3.77 (m, 1 H) 3.94 (s, 3 H) 4.02-4.13 (m, 1 H) 6.20-6.32 (m, 1 H) 7.42-7.51 (m, 1 H) 7.51-7.65 (m, 4 H) |
| A06 | | | | 1.16-1.24 (m, 2 H) 1.32-1.39 (m, 2 H) 2.50 (s, 3 H) 3.56 (d, 2 H) 3.70 (d, 1 H) 4.03-4.20 (m, 1 H) 6.26 (m, 1 H) 7.44-7.67 (m, 5 H) |
| A07 | J | 1.65 | 598.4 | |
| A08 | J | 1.48 | 480.4 | |
| A09 | J | 1.65 | 574.3 | |
| A10 | J | 1.47 | 506.3 | |
| A11 | J | 1.49 | 512.4 | |
| A12 | J | 1.61 | 522.4 | |
| A13 | J | 1.51 | 476.4 | |
| A14 | J | 1.54 | 496.3 | |
| A15 | J | 1.58 | 516.3 | |
| A16 | J | 1.57 | 564.4 | |
| A17 | J | 1.59 | 560.3 | |
| A18 | J | 1.58 | 574.3 | |
| A19 | J | 1.58 | 550.3 | |
| A20 | J | 1.46 | 496.4 | |
| A21 | J | 1.66 | 550.3 | |
| A22 | J | 1.59 | 534.3 | |
| A23 | J | 1.67 | 594.2 | |
| A24 | J | 1.6 | 578.3 | |
| B01 | | | | 1.05-1.19 (m, 2 H) 1.66-1.78 (m, 2 H) 2.46 (s, 3 H) 3.70 (d, H) 3.78 (d, H) 4.01-4.16 (m, 1 H) 6.51 (t, 1 H) 7.43 (d, 1 H) 7.50-7.66 (m, 4 H) 8.53 (br. s., 1 H). |
| B02 | | | | 1.06-1.17 (m, 2 H) 1.68-1.77 (m, 2 H) 2.46 (s, 3 H) 3.71 (d, 1 H) 3.77 (d, 2 H) 4.03-4.13 (m, 1 H) 6.53 (t, 1 H) 7.37-7.47 (m, 2 H) 7.48-7.57 (m, 4 H) 7.57-7.67 (m, 1 H) 8.57 (br. s., 1 H) |

TABLE A1-continued (analytic data of the compounds of Table A):

| Compound number | LC-MS Method | RT (min) | [M + H]⁺ | ¹H NMR (400 MHz, CHLOROFORM-d) δ ppm |
|---|---|---|---|---|
| C01 | | | | 0.84-0.94 (m, 2 H) 1.27-1.35 (m, 2 H) 2.47 (s, 3 H) 3.60-3.76 (m, 3 H) 4.03-4.13 (m, 1 H) 6.44 (t, 1 H) 7.36-7.46 (m, 1 H) 7.48-7.55 (m, 2 H) 7.59 (d, 2 H) |
| C02 | | | | 0.81-0.96 (m, 2 H) 1.28-1.35 (m, 2 H) 2.47 (s, 3 H) 3.60-3.77 (m, 3 H) 4.03-4.12 (m, 1 H) 6.43 (t, 1 H) 7.37-7.47 (m, 2 H) 7.48-7.59 (m, 4 H) |

TABLE B1

(analytic data of the compounds of Table B):

| Compound number | LC-MS Method | RT (min) | [M + H]⁺ | ¹H NMR (400 MHz, CHLOROFORM-d) δ ppm |
|---|---|---|---|---|
| D01 | J | 1.56 | 483.3 | |
| D02 | J | 1.53 | 497.4 | |
| E01 | | | | 0.96-1.13 (m, 1 H) 1.21-1.46 (m, 3 H) 1.63 (d, 3 H) 2.66 (s, 3 H) 3.72 (d, 1 H) 4.11 (d, 1 H) 4.59 (q, 1 H) 7.52-7.65 (m, 4 H) 8.04 (d, 1 H) |

TABLE F1

(analytic data of the compounds of Table F):

| Compound number | ¹H NMR |
|---|---|
| F01 | 1H NMR (400 MHz, CDCl3) δ ppm 7.60 (d, 2 H) 7.55 (s, 1 H) 7.50-7.53 (m, 1 H) 7.30 (d, 1 H) 4.12 (q, 2 H) 4.03-4.09 (m, 3 H) 3.69 (d, 1 H) 2.40 (s, 3 H) 1.32-1.39 (m, 2 H) 1.21-1.31 (m, 2 H) 1.10 (t, 3 H) |
| F02 | ¹H NMR (400 MHz, CDCl3) δ ppm 7.71 (d, 1 H) 7.64 (s, 1 H) 7.56-7.62 (m, 3 H) 4.11 (d, 1 H) 3.71 (d, 1 H) 3.60 (s, 2 H) 2.44 (s, 3 H) 1.41 (s, 9 H) 1.20-1.27 (m, 2 H) 0.96-0.98 (m, 2 H) |
| F03 | ¹H NMR (400 MHz, CDCl3) δ ppm 7.60 (m, 3 H) 7.52-7.57 (m, 1 H) 7.49-7.52 (m, 1 H) 4.10 (d, 1 H) 4.05 (s, 2 H) 3.70 (d, 1 H) 2.51 (s, 3 H) 1.38-1.47 (m, 1 H) 1.30-1.38 (m, 2 H) 1.15-1.24 (m, 2 H) 1.06 (br t, 2 H) 0.67 (br d, 2 H) |
| F04 | 1H NMR (400 MHz, CDCl3) δ ppm 7.60 (d, 2 H) 7.55 (s, 1 H) 7.50-7.54 (m, 1 H) 7.29 (d, 1 H) 4.10 (d, 1 H) 4.06 (s, 2 H) 3.64-3.73 (m, 4 H) 2.40 (s, 3 H) 1.32-1.40 (m, 2 H) 1.20-1.32 (m, 2 H) |
| F05 | 1H NMR (400 MHz, CDCl3) δ ppm 7.60 (d, 2 H) 7.52 (s, 1 H) 7.50 (br d, 1 H) 7.30-7.26 (m, 1 H) 4.05-4.16 (m, 1 H) 3.84 (s, 3 H) 3.65-3.74 (m, 1 H) 2.39 (s, 3 H) 1.39 (br s, 2 H) 1.22 (br s, 2 H) |
| F06 | 1H NMR (400 MHz, CDCl3) δ ppm 7.60 (d, 2 H) 7.57 (s, 1 H) 7.54 (d, 1 H) 7.34 (d, 1 H) 5.17-5.45 (m, 2 H) 4.06-4.15 (m, 1 H) 3.78 (br s, 2 H) 3.70 (d, 1 H) 2.55 (dt, 1 H) 2.41 (s, 3 H) 1.33-1.41 (m, 2 H) 1.20-1.29 (m, 2 H) 1.16 (d, 6 H) |
| F07 | 1H NMR (400 MHz, CDCl3) δ ppm 7.60 (d, 2 H) 7.57 (s, 1 H) 7.52-7.56 (m, 1 H) 7.34 (d,, 1 H) 5.17-5.45 (m, 2 H) 4.11 (d,, 1 H) 3.77 (br s, 2 H) 3.70 (d, 1 H) 2.40 (s, 3 H) 2.07 (s, 3 H) 1.35-1.41 (m, 2 H) 1.19-1.29 (m, 2 H) |
| F08 | 1H NMR (400 MHz, CDCl3) δ ppm 7.60 (d, 2 H) 7.56 (s, 1 H) 7.51-7.55 (m, 1 H) 7.35 (d, 1 H) 4.53-4.79 (m, 2 H) 4.11 (d, 1 H) 3.76 (br s, 2 H) 3.70 (d, 1 H) 3.27 (q, 2 H) 2.40 (s, 3 H) 1.36 (br s, 2 H) 1.21-1.32 (m, 2 H) 1.12 (t, 3 H) |
| F09 | ¹H NMR (400 MHz, CDCl3) δ ppm 7.60 (d, 2 H) 7.56 (s, 1 H) 7.53 (br d, 1 H) 7.35 (d, 1 H) 4.62 (br s, 2 H) 4.11 (d, 1 H) 3.75 (br s, 2 H) 3.70 (d, 1 H) 3.14 (s, 3 H) 2.40 (s, 3 H) 1.36 (br s, 2 H) 1.17-1.31 (m, 2 H) |
| F10 | ¹H NMR (400 MHz, CDCl3) δ ppm 7.60 (d, 2 H) 7.57 (s, 1 H) 7.54 (d, 1 H) 7.34 (d, 1 H) 5.16-5.46 (m, 2 H) 4.11 (d, 1 H) 3.78 (br s, 2 H) 3.70 (d, 1 H) 2.42 (s, 3 H) 1.39 (br s, 2 H) 1.21-1.28 (m, 2 H) 1.19 (s, 9 H) |
| F11 | ¹H NMR (400 MHz, CDCl3) δ ppm 7.60 (d, 2 H) 7.57 (s, 1 H) 7.51-7.56 (m, 1 H) 7.35 (d, 1 H) 5.65 (s, 2 H) 4.04-4.16 (m, 3 H) 3.70 (d, 1 H) 2.42 (s, 3 H) 1.35-1.46 (m, 2 H) 1.18-1.33 (m, 2 H) |
| F12 | ¹H NMR (400 MHz, CDCl3) δ ppm 7.33-7.64 (m, 5 H) 4.61-5.41 (m, 2 H) 4.10 (d, 1 H) 3.45-3.83 (m, 6 H) 2.57-3.29 (m, 3 H) 2.32-2.53 (m, 3 H) 0.76-1.38 (m, 4 H) |

BIOLOGICAL EXAMPLES

These Examples illustrate the pesticidal/insecticidal properties of compounds of formula (I).
Tests were performed as follows:

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A01, A02, A03, A04, A05, A06, A07, A08, A09, A10, A11, A12, A13, A14, A15, A16, A17, A18, A19, A20, A21, A22, A23, A24, B01, B02, C01, C02, D01, D02, F01, F02, F03, F04, F05, F06, F07, F08, F09, F10, F11, F12.

Example B2: *Myzus persicae* (Green Peach Aphid)

Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:
A01, A02, A03, A04, A06, A07, A08, A09, A10, A12, A15, A16, A17, A18, A19, A20, A21, A22, A24, B01, B02, C01, C02, D02, F02, F03, F05, F06, F07, F08, F09, F10, F11.

Example B3: *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A01, A02, A03, A04, A05, A06, A07, A08, A09, A10, A11, A12, A13, A14, A15, A16, A17, A18, A19, A20, A21, A22, A23, A24, B01, B02, $C_{01}$, $C_{02}$, D01, D02, E01, F01, F02, F03, F04, F05, F06, F07, F08, F09, F10, F11, F12.

Example B4: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
A01, A02, A03, A04, A05, A06, A07, A08, A09, A10, A11, A12, A13, A14, A15, A16, A17, A18, A19, A20, A21, A22, A23, A24, B01, B02, $C_{01}$, $C_{02}$, D02, E01, F01, F02, F03, F04, F05, F06, F07, F08, F09, F10, F11, F12.

Example B5: *Tetranychus urticae* (Two-Spotted Spider Mite):Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A01, A02, A03, A04, A05, A06, A07, A08, A09, A10, A12, A13, A14, A15, A16, A17, A18, A19, A20, A21, A23, A24, B01, B02, C01, C02, D02, F01, F02, F03, F04, F05, F06, F07, F08, F09.

Example B6: *Thrips tabaci* (Onion *Thrips*) Feeding/Contact Activity

Sunflower leaf discs were placed on agar in 24-well microtiter plates and sprayed with aqueous test solutions prepared from 10'000 ppm DMSO stock solutions. After drying the leaf discs were infested with a thrips population of mixed ages. The samples were assessed for mortality 6 days after infestation.

The following compounds resulted in at least 80% mortality at an application rate of 200 ppm:
A01, A02, A03, A04, A05, A06, A07, A08, A09, A12, A13, A14, A15, A16, A17, A18, A19, A20, A21, A22, A23, A24, B01, B02, C01, C02, D01, D02, E01 F01, F02, F03, F04, F05, F06, F07, F08, F10.

The invention claimed is:
1. A compound of formula (I),

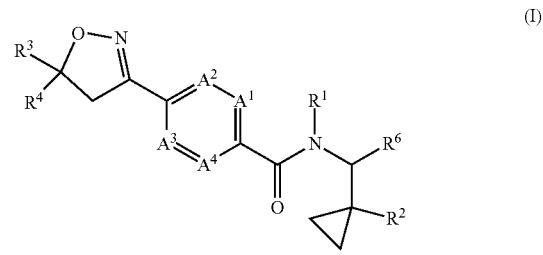

wherein
$A^1$, $A^2$, $A^3$ and $A^4$, independently of one another, are C—H, C—$R^5$ or nitrogen;
$R^1$ is $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl,
$C_1$-$C_8$alkylaminocarbonyl$C_1$-$C_8$alkyl,
$C_1$-$C_8$dialkylaminocarbonyl$C_1$-$C_8$alkyl or
$C_1$-$C_8$alkoxycarbonyl$C_1$-$C_8$alkylamino$C_1$-$C_8$alkyl,
wherein each alkyl or alkoxy group may be optionally substituted with from one to three halogen atoms;

$R^2$ is cyano, C(S)NH$_2$ or C(O)NH$_2$;

$R^3$ is $C_1$-$C_8$haloalkyl;

$R^4$ is aryl, aryl substituted by one to three $R^7$, heteroaryl or heteroaryl substituted by one to three $R^7$;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge, a —CH$_2$—CH$_2$—CH$_2$— bridge, a —CH(OH)—CH$_2$—CH$_2$— bridge, a —C(O)—CH$_2$—CH$_2$— bridge or a —N=CH—CH=CH— bridge;

$R^6$ is hydrogen or $C_1$-$C_8$alkyl; and $R^7$ is independently halogen, cyano, nitro, $C_1$-$C_8$alkyl, $C_1$-$C_8$haloalkyl, $C_1$-$C_8$alkoxy, $C_1$-$C_8$haloalkoxy;

and agrochemically acceptable salts, stereoisomers, enantiomers, tautomers and N-oxides of those compounds.

2. A compound of formula (I) according to claim 1, wherein $R^1$ is $C_1$-$C_8$alkoxy-$C_1$-$C_8$alkyl, $C_1$-$C_8$alkoxycarbonyl or $C_1$-$C_8$alkylcarbonyloxy$C_1$-$C_8$alkyl.

3. A compound of formula (I) according to claim 2, wherein $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl.

4. A compound of formula (I) according to claim 1, wherein $R^2$ is cyano.

5. A compound of formula (I) according to claim 1, wherein $R^2$ is C(S)NH$_2$ or C(O)NH$_2$.

6. A compound of formula (I) according to claim 1, wherein $R^3$ is $C_1$-$C_4$haloalkyl.

7. A compound of formula (I) according to claim 1, wherein $R^4$ is aryl, aryl substituted by one to three $R^7$, 5-6 membered heteroaryl or 5-6 membered heteroaryl substituted by one to three $R^7$.

8. A compound of formula (I) according to claim 1, wherein $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl.

9. A compound of formula (I) according to claim 1, wherein $R^7$ is independently halogen, cyano, $C_1$-$C_4$alkyl, $C_1$-$C_4$haloalkyl, $C_1$-$C_4$alkoxy or $C_1$-$C_4$haloalkoxy.

10. A compound of formula (I) according to claim 1, wherein $R^6$ is hydrogen.

11. A compound of formula (Int-II)

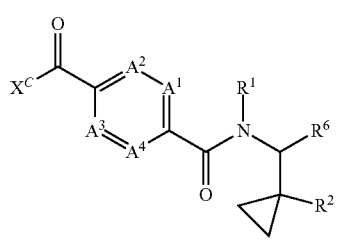

(Int-II)

$A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl,
wherein each alkyl or alkoxy group may be optionally substituted with from one to three halogen atoms or with a cyano group;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge, a —CH$_2$—CH$_2$—CH$_2$— bridge, a —CH(OH)—CH$_2$—CH$_2$— bridge, a —C(O)—CH$_2$—CH$_2$— bridge or a —N=CH—CH=CH— bridge;

$R^6$ is hydrogen or $C_1$-$C_8$alkyl;

$R^2$ is cyano, C(S)NH$_2$, C(O)OH or C(O)NH$_2$; $X^c$ is CH$_2$-halogen, CH=C($R^3$)$R^4$ or CH$_2$C(OH)($R^3$)$R^4$ wherein $R^3$ and $R^4$ are as defined under formula (I) in claim 1; and a salt or N-oxide of a compound of formula (Int-II).

12. A compound of formula (Int-III)

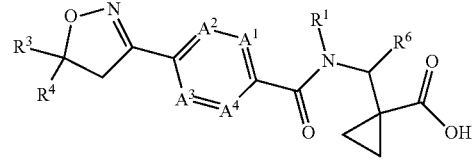

(Int-III)

$A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl,
wherein each alkyl or alkoxy group may be optionally substituted with from one to three halogen atoms or with a cyano group;

$R^3$ is $C_1$-$C_8$haloalkyl;

$R^4$ is aryl, aryl substituted by one to three $R^7$, heteroaryl or heteroaryl substituted by one to three $R^7$;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge, a —CH₂—CH₂—CH₂— bridge, a —CH(OH)—CH₂—CH₂— bridge, a —C(O)—CH₂—CH₂— bridge or a —N=CH—CH=CH— bridge;

$R^6$ is hydrogen or $C_1$-$C_8$alkyl; and $R^7$ is independently halogen, cyano, nitro, $C_1$-$C_8$alkyl, $C_1$-$C_8$haloalkyl, $C_1$-$C_8$alkoxy, $C_1$-$C_8$haloalkoxy;

and a salt or N-oxide of the compound of formula (Int-III).

13. A pesticidal composition, which comprises at least one compound of formula (I) according to claim 1 or, where appropriate, a tautomer thereof, in each case in free form or in agrochemically utilizable salt form, as active ingredient and at least one auxiliary.

14. A method for controlling pests, which comprises applying a composition according to claim 13 to the pests or their environment with the exception of a method for treatment of the human or animal body by surgery or therapy and diagnostic methods practised on the human or animal body.

15. A method for the protection of seeds from the attack by pests, which comprises treating the seeds or the site, where the seeds are planted, with a composition according to claim 13.

16. A compound of formula (I),

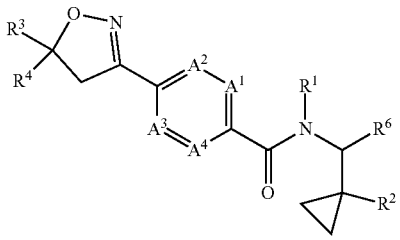

wherein $A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group;

$R^2$ is cyano, C(S)NH₂ or C(O)NH₂;

$R^3$ is $C_1$-$C_8$haloalkyl;

$R^4$ is aryl, aryl substituted by one to three $R^7$, heteroaryl or heteroaryl substituted by one to three $R^7$;

$R^8$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-;

$R^6$ is hydrogen or $C_1$-$C_8$alkyl; and $R^7$ is independently halogen, cyano, nitro, $C_1$-$C_8$alkyl, $C_1$-$C_8$haloalkyl, $C_1$-$C_8$alkoxy, $C_1$-$C_8$haloalkoxy;

and agrochemically acceptable salts, stereoisomers, enantiomers, tautomers and N-oxides of those compounds.

17. The compound of claim 16, wherein $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl.

18. The compound of claim 16, wherein $R^2$ is cyano.

19. The compound of claim 16, wherein $R^2$ is C(S)NH₂ or C(O)NH₂.

* * * * *